United States Patent [19]

Crooke et al.

[11] Patent Number: 5,756,282
[45] Date of Patent: May 26, 1998

[54] OLIGONUCLEOTIDES FOR THE DIAGNOSIS OF PAPILLOMAVIRUS

[75] Inventors: Stanley T. Crooke, Carlsbad; Christopher K. Mirabelli, Encinitas; David J. Ecker; Lex M. Cowsert, both of Carlsbad, all of Calif.

[73] Assignee: Isis Pharmaceuticals, Inc., Carlsbad, Calif.

[21] Appl. No.: 370,517

[22] Filed: Jan. 9, 1995

Related U.S. Application Data

[63] Continuation-in-part of Ser. No. 860,925, Mar. 31, 1992, Pat. No. 5,457,189, continuation-in-part of PCT/US90/07067 Dec. 3, 1990, which is a continuation-in-part of Ser. No. 445,196, Dec. 4, 1989, abandoned.

[51] Int. Cl.$^6$ ............... C12Q 1/70; C12Q 1/68; C07H 21/04; C12P 19/34
[52] U.S. Cl. ............... 435/5; 435/6; 435/91.2; 536/24.3; 536/24.32; 536/24.5; 514/44
[58] Field of Search ............... 435/6, 5, 91.2; 536/24.3, 24.32, 24.5; 514/44

[56] References Cited

U.S. PATENT DOCUMENTS 4,983,728  1/1991  Herzog et al. ............... 536/27

OTHER PUBLICATIONS

Yang et al. PNAS 82:1030–1034, 1985.
Durst et al. PNAS 80: 3812–3815, 1983.
Agrawal and Sarin, "Antisense oligonucleotides: gene regulation and chemotherapy of AIDS", *Adv. Drug Deliv. Rev.* (1991) 6:251–270.
Amtmann, E. & Sauer, G., *J. Virol.* 4:59–66 (1982).
Androphy, E.J., Lowy, D.R. & Schiller, J.T., *Nature* 325, 70–73 (1987).
Baker, C.C. & Howley, P.M., *EMBO J.* 6:1027–1035 (1987).
Boshart, M., Gissmann, L., Ikenberg, H., Kleinheinz, A., Scheurlen, W. & zur Hausen, H., *EMBO J.* 3:1151–1157 (1984).

Chen, E. Y., Howley, P. M., Levinson, A. D., and Seeburg, P. H., "The primary structure and genetic organization of the bovine papillomavirus type 1 genome", *Nature* 299:529–534 (1982).
Chin, M.T., Hirochika, R., Hirochika, H., Broker, T.R. & Chow, L.T., *J. Virol.* 62:2994–3002 (1988).
Cole, S.T. and Danos, O., "Nucleotide Sequence and Comparative Analysis of the Human Papillomavirus Type 18 Genome", *J. Mol. Biol.* 193, 599–608 (1987).
Cole, S.T. and Streeck, R.E., "Genome Organization and Nucleotide Sequence of Human Papillomavirus Type 33, Which Is Associated with Cervical Cancer", *J. Virol.* 58, 991–995 (1986).
Cowsert, L. M., Lake, P., and Jenson, A. B., "Topographical and conformational Epitopes of Bovine Papillomavirus type 1 Defined by Monoclonal Antibodies", *JNCI* 79:1053–1057 (1987).
Dartmann et al., *Virology* 151, 124–130 (1986).
DiMaio, D., *J. Virol.* 57:475–480 (1986).
DiMaio, D. & Settleman, J., *EMBO J.* 7:1197–1204 (1988).
Dürst, M., Gissmann, L., Ikenberg, H. & zur Hausen, H., *Proc. Natl. Acad. Sci. USA* 80:3812–3815 (1983).
Dvoretzky, I. Schober, R., and Lowy, D., "Focus Assay in Mouse Cells for Bovine Papillomavirus type 1", *Virology* 103:369–375 (1980).
Dahlberg, A. E., Digman, C. W. and Peacock, A. C., *J. Mol. Biol.* 41:39 (1969).
Engel, L.W., Heilman, C.A. & Howley, P.M., *J. Virol.* 47:516–528 (1983).

(List continued on next page.)

*Primary Examiner*—Stephanie W. Zitomer
*Assistant Examiner*—Dianne Rees
*Attorney, Agent, or Firm*—Law Offices of Jane Massey Licata

[57] ABSTRACT

Oligonucleotides are provided which are targeted to human papillomavirus E2 transactivator messenger RNA. Such oligonucleotides can be used for diagnostics and therapeutics as well as for research purposes.

4 Claims, 21 Drawing Sheets

E2 TRANSACTIVATOR AUG REGION

```
              2595        2605        2615        2625
               *           *           *           *
        AGGAGGAGGAUAGUGAAGAGGAUGGAGACAGCAUGCGAACGUUAACAU
                    TCACTTCTCCTACCTCTGTCGTACGCTTGC              003
                                  TACCTCTGTCGTACGC              004
                    TCACTTCTCCTACCT                             036
                    TCACTTCTCCTACCTCTG                          037
                    TCACTTCTCCTACCTCTGTCG                       038
                TCCTATCACTTCTCC                                 039
                      TTCTCCTACCTCTGT                           040
                          CCTACCTCTGTCGTA                       041
```

OTHER PUBLICATIONS

Frost, E. and Williams, J., "Mapping Temperature–Sensitive and host–range mutation of Adenovirus type 5 by Marker Rescue", *Virology* 91:39–50 (1978).

Fuchs et al., "Epidermodysplasia Verruciformis–Associated Human Papillomavirus 8: Genomic Sequence and Comparative Analysis", *J. Virol.* 58, 626–634 (1986).

Gennaro, Alfonso, Ed., *Remington's Pharmaceutical Sciences*, 18th Edition 1990. Mack Publishing Co., Easton, PA.

Gissmann, L., Wolnik, L., Ikenberg, H., Koldovsky, U., Schnurch, H.G. & zur Hausen, H., *Proc. Natl. Acad. Sci. USA* 80:560–563 (1983).

Gius, D., Grossman, S., Bedell, M.A. & Laimins, L.A., *J. Virol.* 62:665–672 (1988).

Goldsborough et al. "Nucleotide Sequence of Human Papillomavirus Type 31: A Cervical Neoplasia–Associated Virus", *Virology* 171, 306–311 (1989).

Graham, F. L. and van der Eb, A. J., "A New Technique for the Assay of Infectivity of Human Adenovirus 5 DNA", *Virology* 52:456–461 (1973).

Groff, D.E. & Lancaster, W.D., *Virology* 150:221–230 (1986).

Groman, C.M., Moffat, L.F., and Howard, B.H., *Mol. Cell. Biol.* 2:1044–1051 (1982).

Heilman, C.A., Engel, L., Lowy, D.R. & Howley, P.M., *Virology* 119:22–34 (1982).

Hirochika, H., Broker, T.R. & Chow, L.T., *J. Virol.* 61:2599–2606 (1987).

Herbomel et al., *Cell* 39:653 (1984).

Iyer, R. P., Phillips, L. R., Egan, W., Regan, J. and Beaucage, S. L., "The Automated Synthesis of Sulfur–Containing Oligodeoxyribonucleotides Using $^3$H–1, 2–Bensodithiol–3–one 1,1–Dioxide as a Sulfur–Transfer Reagent", *J. Org. Chem.* 55:4693–4699 (1990).

Iversen, P. 1991. "In vivo studies with phosphorothioate oligonucleotides: pharmacokinetics prologue", *Anticancer Drug Des.* 6:531–538).

Kennedy et al., "A Negative Regulatory Element in the Human Papillomavirus Type 16 Genome Acts at the Level of Late mRNA Stability", *J. Virol.* 65, 2093–2097 (1991).

Lambert, P.F., Spalholz, B.A. & Howley, P.M., *Cell* 50:69–78 (1987).

Maniatis, T., Fritsch, E. F. and Sambrook, *J. Molecular Cloning: A Laboratory Manual*, Cold Spring Harbor Laboratory, New York, 1982.

McBride, A.A., Schlegel, R. & Howley, P.M., *EMBO J.* 7:533–539 (1988).

Moskaluk, C. & Bastia, D., *Proc. Natl. Acad. Sci. USA* 84:1215–1218 (1987).

Phelps, W.C. & Howley, P.M., *J. Virol.* 61:1630–1638 (1987).

Phelps, W. C. Yee, C. L., Munger, K., and Howley, P. M. 1988, "The Human Papillomavirus Type 16 E7 Gene Encodes Transactivation and Transformation Functions Similar to Those of Adenovirus E1A", *Cell* 53:539–547.

Rabson, M.S., Yee, C., Yang, Y.C. & Howley, P.M., *J. Virol.* 60:626–634 (1986).

Sambrook et al., *Molecular Cloning. A Laboratory Manual*, Cold Spring Harbor Laboratory Press, 1989, vol. 2, p. 10.59.

Sarver, N., Rabson, M.S., Yang, Y.C., Byrne, J.C. & Howley, P.M., *J. Virol.* 52:377–388 (1984).

Seedorf et al., "Human Papillomavirus Type 16 DNA Sequence", *Virology* 145, 181–185 (1985).

Spalholz, B.A., Yang, Y.C. & Howley, P.M., *Cell* 42:183–191 (1985).

Spalholtz et al., *J. Virol.* 61:2128–2137 (1987).

Spalholz, B. A., Byrne, J. C. and Howley, P. M., "Evidence for Cooperativity between E2 Binding Sites in E2 trans–regulation of Bovine Papillomavirus Type 1", *J. Virol.* 62:3143–3150 (1988).

Thierry, F. & Yaniv, M., *EMBO J.* 6:3391–3397 (1987).

Yang, Y.–C., Okayama, H. and Howley, P. M., "Bovine papillomavirus contains multiple transforming genes", *Proc. Natl. Acad. Sci. USA* 82:1030–1034 (1985).

Zur Hausen, H. and Schneider, A., *The Papovaviridae*, Eds. N.P. Salzman and P.M. Howley, Plenum Press, New York, 1987, vol. 2, pp. 245–264.

Fig. 3A

```
   1 ATTTGTACTT GCATAGTCGG GTGCAAACCT TTCGCTTTGA GCAGCCATGC ACAGATGAAT
  61 CGGGTGAGCA ACCTTTTAAT ATTACTGATG CAGATTGGAA ATCTTTTTT GTAAGGTTAT
 121 GGGGGCGTTT AGACCTGATT GACGAGGAGG AGGATAGTGA AGAGGATGGA GACAGCATGC
 181 GAACGTTTAC ATGTAGCGCA AGAAACACAA ATGCAGTTGA TTGAGAAAAG TAGTGATAAG
 241 TTGCAAGATC ATATACTGTA CTGGACTGCT GTTAGAACTG AGAACACACT GCTTTATGCT
 301 GCAAGGAAAA AAGGGGTGAC TGTCCTAGGA CACTGCAGAG TACCACACTC TGTAGTTTGT
 361 CAAGAGAGAG CCAAGCAGGC CATTGAAATG CAGTTGTCTT TGCAGGAGTT AAGCAAAACT
 421 GAGTTTGGGG ATGAACCATG GTCTTTGCTT GACACAAGCT GGGACCGATA TATGTCAGAA
 481 CCTAAACGGT GCTTTAAGAA AGGCGCCAGG GTGGTAGAGG TGGAGTTTGA TGGAAATGCA
 541 AGCAATACAA ACTGGTACAC TGTCTACAGC AATTTGTACA TGCGCACAGA GGACGGCTGG
 601 CAGCTTGCGA AGGCTGGGGC TGACGGAACT GGGCTCTACT ACTGCACCAT GGCCGGTGCT
 661 GGACGCATTT ACTATTCTCG CTTTGGTGAC GAGGCAGCCA GATTAGTAC AACAGGGCAT
 721 TACTCTGTAA GAGATCAGGA CAGAGTGTAT GCTGGTGTCT CATCCACCTC TTCTGATTTT
 781 AGAGATCGCC CAGACGGAGT CTGGGTCGCA TCCGAAGGAGA CCCTGCAGGA
 841 AAAGAAGCCG AGCCAGCCCA GCCTCGGTTG TCTTTGCTCG GTCCCTCGCT CGCACCCCTA CAATTTCCT
 901 ATCAGAGCAG GCCTCGGTTG GGTACGGGAC GGTCCCTCGCT CGCACCCCTA CAATTTCCT
 961 GCAGGCTCGG GGGCTCTAT TCTCCGCTCT TCCTCCACCC CGGTGCAGGG CACGGTACCG
1021 GTGGACTTGG CATCAAGGCA GGAAGAAGAG GAGCAGTCGC CCGACTCCAC AGAGGAAGAA
1081 CCAGTGACTC TCCCAAGGCG CACCACCAAT GATGGATTCC ACCTGTTAAA GGCAGGAGGG
1141 TCATGCTTTG CTCTAATTTC AGAACTGCT AACCAGTAA AGTGCTATCG CTTTCGGGTG
1201 AAAAGAACC ATAGACATCG CTACGAGAAC TGCACCACCA CCTGGTTAC AGTTGCTGAC
1261 AACGGTGCTG AAAGACAAGG ACAAGCACAA ATACTGATCA CCTTTGGATC GCCAAGTCAA
```

```
1321 AGGCAAGACT TTCTGAAACA TGTACCACTA CCTCCCTGGAA TGAACATTTC CGGCTTTACA
1381 GCCAGCTTGG ACTTCTGATC ACTGCCATTG CCTTTCTTC ATCTGACTGG TGTACTATGC
1441 CAAATCTATG GTTCTATTG TTCTTGGGAC TAGTTGCTGC AATGCAACTG CTGCTATTAC
1501 TGTTCTTACT CTTGTTTTT CTTGTATACT GGGATCATTT TGAGTGCTCC TGTACAGGTC
1561 TGCCCTTTA ATGCCTTTAC ATCACTGGCT ATTGGCTGTG TTTTACTGT TGTGTGGATT
1621 TGATTTGTTT TATATACTGT ATGAAGTTT TCATTTGTG CTTGTATTGC TGTTTGTAAG
1681 TTTTTTACTA GAGTTTGTAT TCCCCCTGCT CAGATTTTAT ATGGTTTAAG CTGCAGCAAT
1741 AAAAATGAGT GCACGAAAAA G
```

*Fig. 3B*

```
  1 ATTTGTACTT GCATAGTCGG GTGCAAACCT TTCGCTTTGA GCAGCCATGC ACAGATGAAT
 61 CGGGTGAGCA ACCTTTTAAT ATTACTGATG CAGATTGGAA ATCTTTTTTT GTAAGGTTAT
121 GGGGGCGTTT AGACCTGATT GACGAGGAGG AGGATAGTGA AGAGGATGGA GACAGCATGC
181 GAACGTTTAC ATGTAGCGCA AGAAACACAA ATGCAGTTGA TTGAGAAAAG TAGTGATAAG
241 TTGCAAGATC ATATACTGTA CTGGACTGCT GTTAGAACTG AGAACACACT GCTTTATGCT
301 GCAAGGAAAA AAGGGGTGAC TGTCCCTAGGA CACTGCAGAG TACCACACTC TGTAGTTTGT
361 CAAGAGAGAG CCAAGCAGGC CATTGAAATG CAGTTGTCTT TGCAGGAGTT AAGCAAAACT
421 GAGTTTGGGG ATGAACCATG GTCTTTGCTT GACACAAGCT GGGACCGATA TATGTCAGAA
481 CCTAAACGGT GCTTTAAGAA AGGCGCCAGG GTGGTAGAGG TGGAGTTTGA TGGAAATGCA
541 AGCAATACAA ACTGGTACAC TGTCTACAGC AATTTGTACA TGCCGCACAGA GGACGGCTGG
601 CAGCTTGCGA AGGCTGGGGC TGACGGAACT GGGCTCTA
```

```
         2443              2581  2608              3082              3837       4203
          |                 |     |                 |                 |          |
          |_____|     |_____|_____|_____|
          001     011              003 013 015  005  017       019        007  009
                                              E2 ORF
```

| Oligo | 5'------------------3' | Comments |
|---|---|---|
| LC001.ABI | AGGTTTGCACCCGACTATGCAAGTACAAAT | mRNA cap region |
| LC002.ABI | TATGCAAGTACAAAT | mRNA cap region |
| LC003.ABI | CGTTCGCATGCTGTCTCCATCCTCTTCACT | initiation of translation |
| LC004.ABI | GCATGCTGTCTCCAT | initiation of translation |
| LC005.ABI | AAATGGGTCCAGCACCGGCCATGGTGCAGT | transrepressor start |
| LC006.ABI | AGCACCGGCCATGGT | transrepressor start |
| LC007.ABI | CAATGGCAGTGATCAGAAGTCCAAGCTGGC | translational termination |
| LC008.ABI | GCAGTGATCAGAAGT | translational termination |
| LC009.ABI | ATTGCTGCAGCTTAAACCATATAAAATCTG | 3' untranslated region |
| LC010.ABI | CTTAAACCATATAAA | 3' untranslated region |
| LC011.ABI | AAAAAAGATTTCCAATCTGCATCAGTAAT | 5' untranslated region |
| LC012.ABI | AAGATTTCCAATCTG | 5' untranslated region |
| LC013.ABI | CAGTGTCCTAGGACAGTCACCCCTTTTTC | 5' coding region |
| LC014.ABI | GGACAGTCACCCCTT | 5' coding region |
| LC015.ABI | TGTACAAATTGCTGTAGACAGTGTACCAGT | mid coding region |
| LC016.ABI | GCTGTAGACAGTGTA | mid coding region |
| LC017.ABI | GTGGGAGCGAGGACCGTCCCGTACCCAACC | 3' coding region |
| LC018.ABI | GGACCGTCCCGTACC | 3' coding region |
| LC019.ABI | TTTAACAGGTGGAATCCATCATTGGTGGTG | 5' coding region |
| LC020.ABI | GGAATCCATCATTGG | 5' coding region |

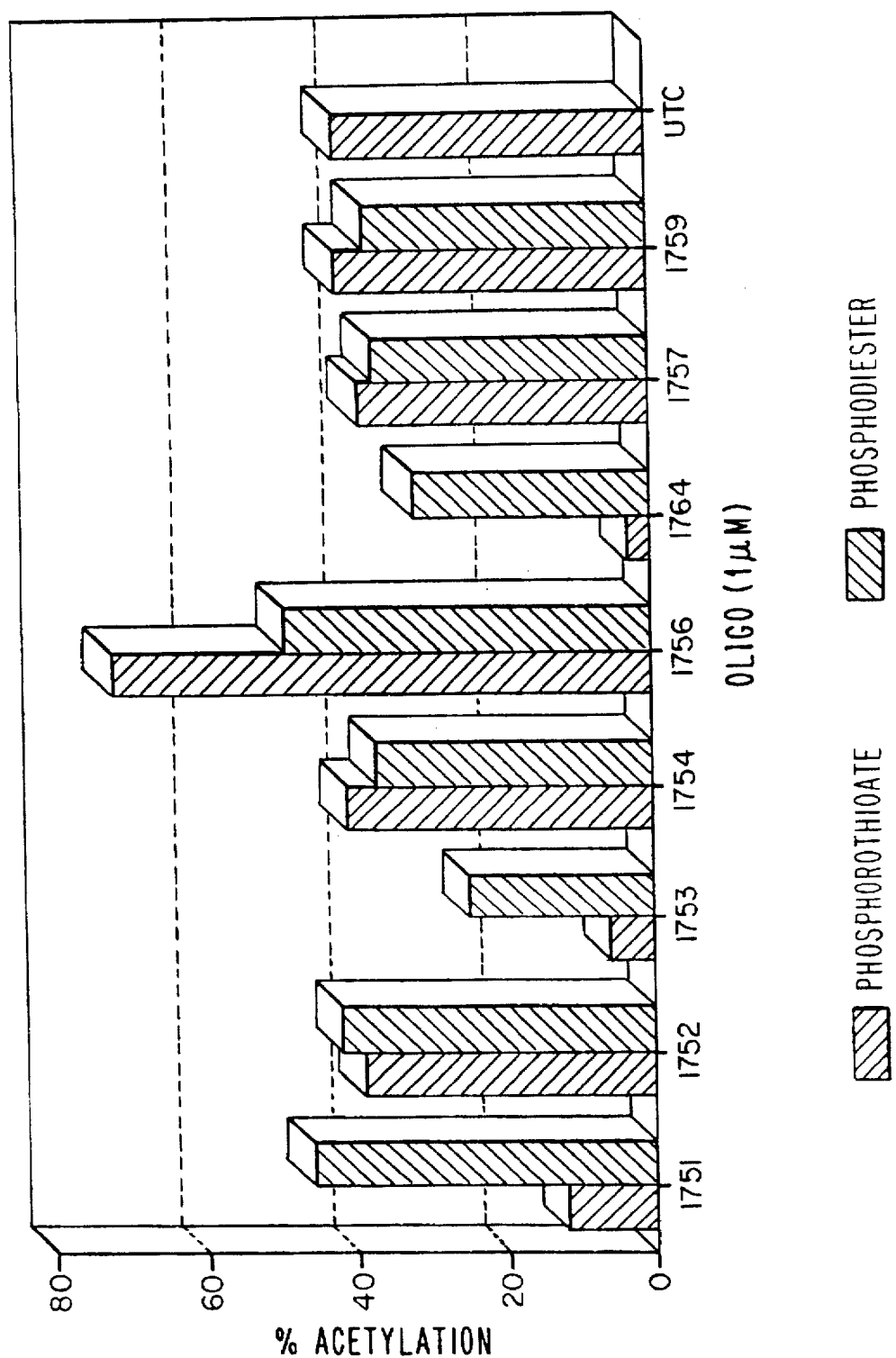

E2 TRANSACTIVATOR AUG REGION

```
        2595      2605      2615      2625
         *         *         *         *
AGGAGGAGGAUAGUGAAGAGGAUGGAGACAGCAUGGCGAACGUUAACAU    003
        TCACTTCTCCTACCTTCTGTCGTACGCTTGC              004
        TCACTTCTCCTACCT                              036
        TCACTTCTCCTACCTCCTCTG                        037
        TCACTTCTCCTACCTCCTCTCG                       038
        TCACTTCTCCTACCTCCTGTCG                       039
        TCCTATCACTTCTCC                              040
               TTCTCCTACCTCTGT                       041
                 CCTACCTCTGTCGTA
```

*Fig. 8A*

E2 TRANSREPRESSOR AUG REGION

```
        3080      3090      3100      3110
         *         *         *         *
ACUGGGCUCUACUACUGCACCAUGGCCCGUCGUCGGACGCAUUACUA      005
        TGACGTGGTACCGGCCACGACCTGCCGTAAA              006
        TGGTACCGGCCACGA                              042
        ACGTGGTACCGGCCA                              043
        ATGACGTGGTACCGG                              044
        TGATGACGTGGTACC                              045
        GAGATGATGACGTGG
```

*Fig. 8B*

```
                    E2_First_Methionine
  2710       2720   |        2730           2740            2750
   *          *     |         *              *               *
 GAT TCA GAG GAC GAG GAA GAT GGA AGC AAT AGC CAA GCG TTT AGA TGC GTG C
 CTA AGT CTC CTG CTT CTA CCT TCG TTA TCG GTT CGC AAA TCT ACG CAC G
  D   S   E   D   E   E   D   G   S   N   S   Q   A   F   R   C   V
 ┌─┬───┐ c   c   c   c   c   c   c   c                       c   c  c┐
 │d│ I │ d   d   d   d   d   d   d   d                       c   c  c│
 └─┴───┘                         ┌───┬───┬───┬───┬───┬───┐   ┌───┬───┤
                                 │ M │ E │ A │ I │ A │ K │ R │ L │ D │A│C│
                                 │ d │ d │ d │ d │ d │ d │ d │ d │ d │d│d│
                                         E1 ORF                    E2 ORF
```

OLIGONUCLEOTIDES FOR THE DIAGNOSIS OF PAPILLOMAVIRUS

This is a continuation-in-part application of U.S. Ser. No. 07/860,925, filed Mar. 31, 1992 now U.S. Pat. No. 5,457, 189, which is a CIP of PCT/US90/07067, filed Dec. 3, 1990, which is a CIP of U.S. Ser. No. 07/445,196 filed Dec. 4, 1989, now abandoned, entitled "Antisense Oligonucleotide Inhibition of Papillomavirus", each of which is assigned to the assignee of the preset invention.

FIELD OF THE INVENTION

This invention relates to the diagnosis and treatment of infections in animals caused by papillomavirus using oligonucleotides targeted to human papillomavirus E2 transactivator mRNA. This invention is also directed to the detection and quantitation of papillomavirus in samples suspected of containing it by contacting these samples with an oligonucleotide of the present invention. Specifically, this invention is directed to oligonucleotides targeted to human papillomavirus E2 transactivator mRNA. Such oligonucleotides can also be used as research reagents and for kits both for research and for diagnosis.

BACKGROUND OF THE INVENTION

The papillomaviruses (PV) are widespread in nature and are generally associated with benign epithelial and fibroepithelial lesions commonly referred to as warts. They have been detected in and isolated from a variety of higher vertebrates including humans, cattle, rabbits, deer and several avian species. Although these viruses are generally associated with benign lesions, a specific subset of the viruses have been associated with lesions that may progress to carcinomas. The implication that these viruses may play an etiologic role in the development of some human cancers follows from numerous studies that have shown the presence of transcriptionally active human papillomavirus (HPV) deoxyribonucleic acids in a high percentage of certain cancerous lesions. Zur Hausen, H. and Schneider, A. 1987. In: The Papovaviridae, vol. 2, edited by N. P. Salzman and P. M. Howley, pp. 245–264. Plenum Press, New York.

In man, human papillomaviruses cause a variety of diseases including common warts of the hands and feet, laryngeal warts and genital warts. More than 57 types of HPV have been identified so far, many of which the complete genome sequences have been published. The gene sequences for several HPV's have been determined and are provided in GenBank. For example, the complete genome for HPV-11 was published by Dartmann et al., *Virology* 151, 124–130 (1986) and is listed in GenBank under Accession No. M14119. The complete genome for HPB-6 was published by Schwarz et al., *EMBO J.* 2, 2341–2348 (1983) and is listed in GenBank under Accession No. X00203. The complete genome for HPV-8 was published by Fuchs et al., *J. Virol.* 58, 626–634 (1986) and is listed under GenBank Accession No. M12737. The complete genome for HPV-16 was published by Seedork et al., *Virology* 145, 181–185 (1985) and by Kennedy et al., *J. Virol.* 65, 2093–2097 (1991) and is listed under GenBank Accession No. K02718. The complete genome for HPV-18 was published by Cole, S. T. and Danos, O., *J. Mol. Biol.* 193, 599–608 (1987) and is listed under GenBank Accession No. X05015. The complete genome for HPV-31 was published by Goldsborough et al. *Virology* 171, 306–311 (1989) and is listed under GenBank Accession No. J04353. The complete genome for HPV-33 was published by Cole, S. T. and Streeck, R. E., *J. Virol.* 58, 991–995 (1986) and is listed under GenBank Accession No. M12732. Each HPV type has a preferred anatomical site of infection; each virus can generally be associated with a specific lesion. Genital warts, also referred to as venereal warts and condylomata acuminata, are one of the most serious manifestations of PV infection. As reported by the Center for Disease Control, the sexual mode of transmission of genital warts is well established and the incidence of genital warts is on the increase. The seriousness of genital warts is underlined by the recent discovery that HPV DNA can be found in all grades of cervical intraepithelial neoplasia (CIN I-III) and that a specific subset of HPV types can be found in carcinoma in situ of the cervix. Consequently, women with genital warts, containing specific HPV types are now considered at high risk for the development of cervical cancer. Current treatments for genital warts are inadequate.

There is a great, but as yet unfulfilled, desire to provide compositions of matter which can be used in the diagnosis and treatment of papillomavirus infections in animals. Additionally, improved kits and research reagents for use in the study of papillomavirus are needed.

OBJECTS OF THE INVENTION

It is an object of this invention to provide oligonucleotides targeted to the human papillomavirus E2 transactivator mRNA. Such oligonucleotides of the present invention are useful as diagnostics and therapeutics for papillomavirus in humans.

BRIEF DESCRIPTION OF THE DRAWINGS

FIGS. 3a and 3b are nucleotide sequences of the BPV-1 E2 transactivator gene mRNA showing nucleotides 2443 through 4203.

FIG. 4 is a nucleotide sequence of the BPV-1 E2 transactivator gene mRNA showing the domain having nucleotides 2443 through 3080.

FIG. 5 is the nucleotide sequences of antisense oligonucleotides made in accordance with the teachings of the invention and the relative position of the oligonucleotides on the E2 mRNA. The oligonucleotide identifier, sequence and functional role are depicted.

FIG. 6 is a graphical depiction of the effects of antisense oligonucleotides made in accordance with the teachings of the invention on E2 expression. Oligonucleotides targeted to the mRNA CAP region (I1751) and the translation codon for the E2 transactivator (I1753) are shown to reduce E2 transactivation at micromolar concentrations.

FIGS. 8A and 8B are the nucleotide sequences of antisense oligonucleotides made in accordance with the teachings of the invention targeted to the transactivator and transrepressor regions of the E2 mRNA.

FIG. 15 is the nucleotide sequence of HPV-11 in the region of the translation initiation codon of E2.

SUMMARY OF THE INVENTION

Figure 1A:
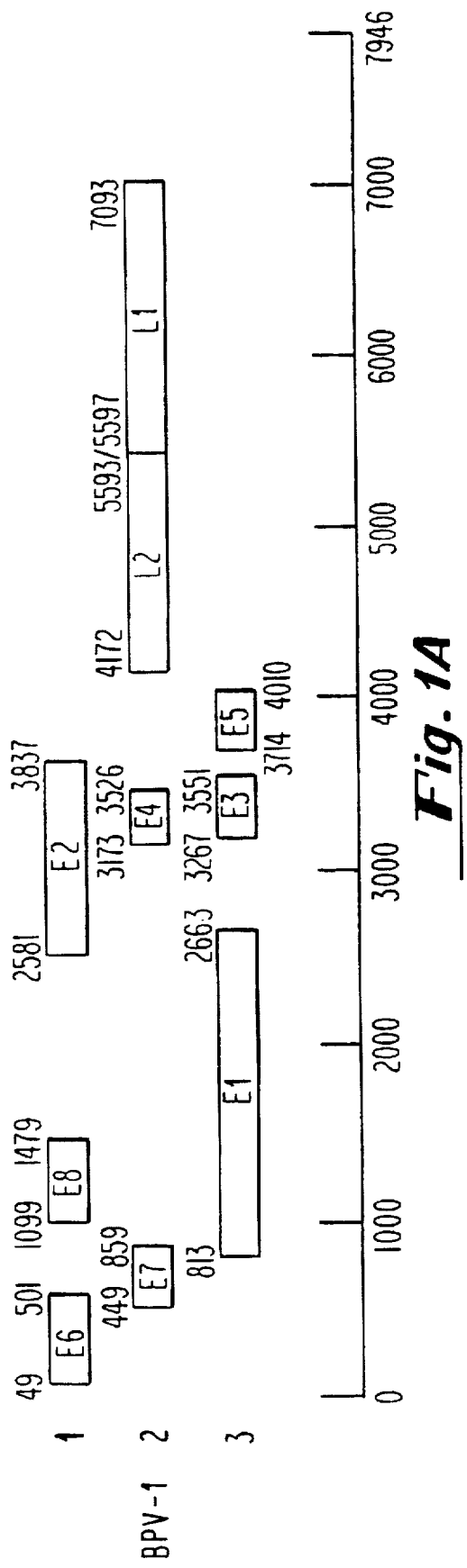
FIGS. 1a, 1b, 1c and 1d, are schematic maps of the genetic organization of several PV genomes.
Figure 1B:
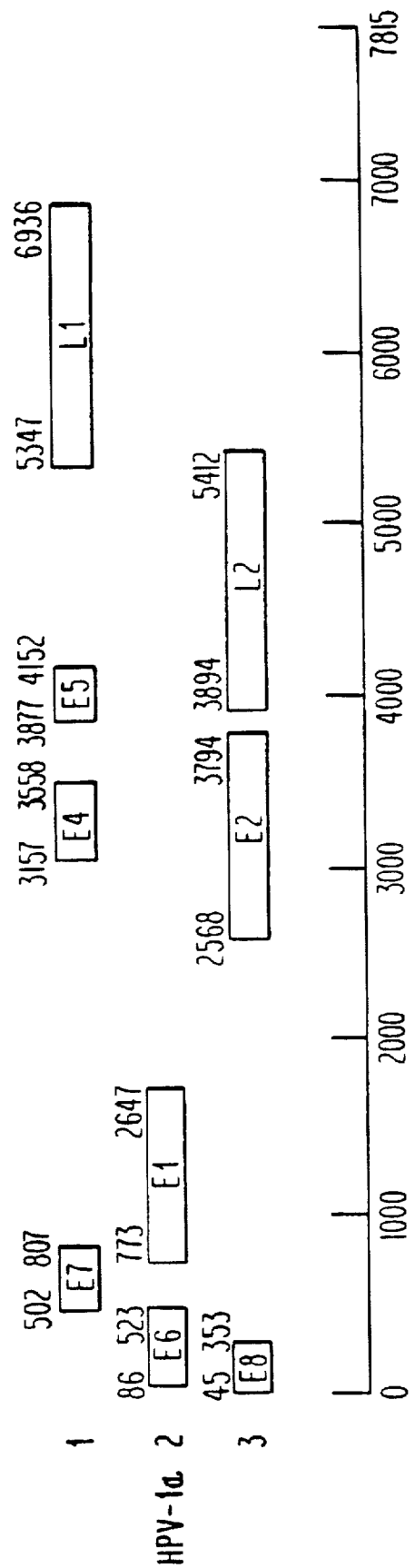
Figure 1C:
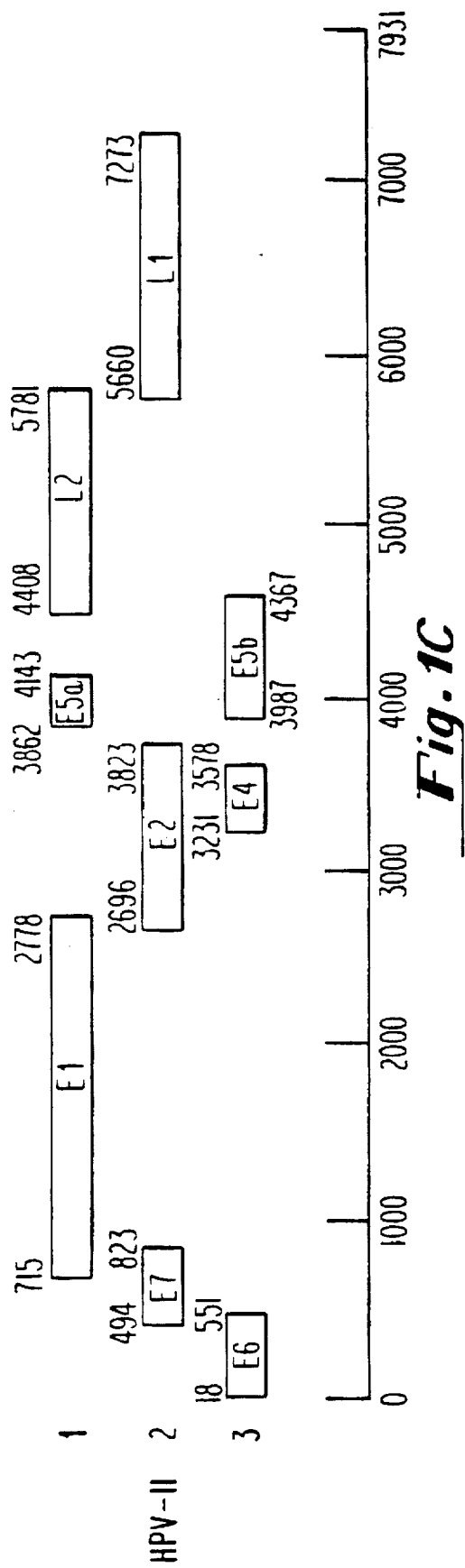
Figure 1D:
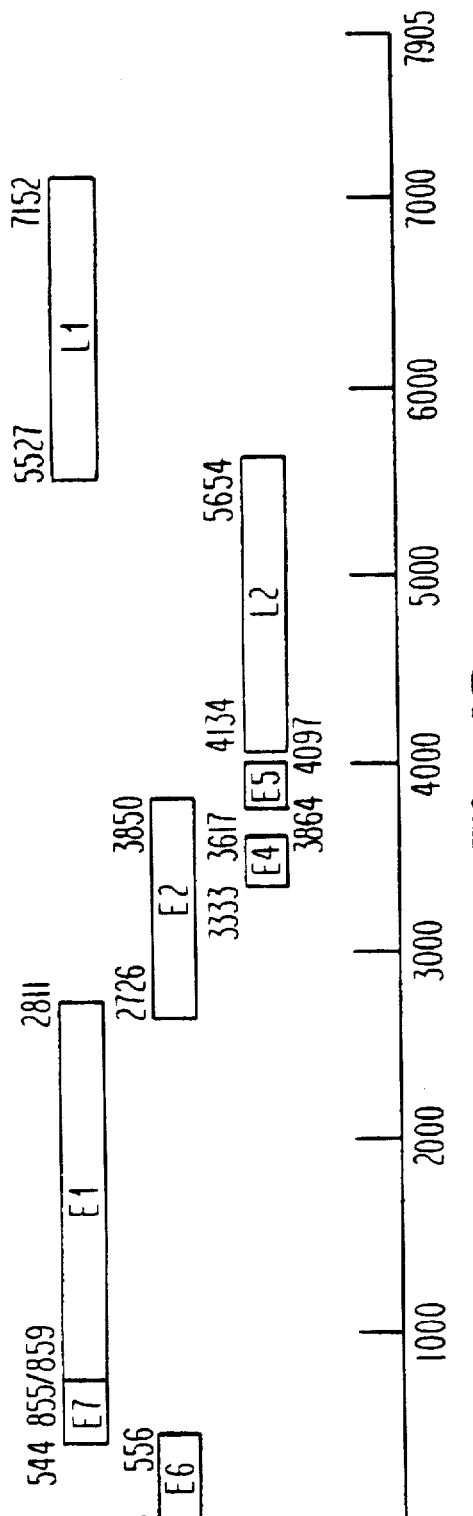

In accordance with preferred embodiments of this invention, oligonucleotides are provided which are targeted to human papillomavirus E2 transactivator region. The oligonucleotides of the present invention can be used in the diagnosis and treatment of papillomavirus.

It has been found that genital warts of specific HPV types place infected women at high risk for the development of cervical cancer. The oligonucleotides of the present invention can be used in the early detection and diagnosis of these types of HPV, thus allowing for more effective preventative care.

In addition, the oligonucleotides of the present invention can be used to treat papillomavirus infection. When used as therapeutics, the oligonucleotides do not alter the genetic code as in gene therapy, but rather modify the expression of a papillomavirus to produce a pharmacological effect. The oligonucleotides are able to inhibit the function of the RNA, either its translation into protein, its translocation into the cytoplasm, or any other activity necessary to its overall biological function. The failure of the messenger RNA to perform all or part of its function results in failure of the papillomavirus genome to be properly expressed; multiplication fails, correct progeny are not formed in effective numbers, and the deleterious effects of those progeny upon animals infected with the papillomavirus are modulated.

It has now been found to be preferred to target a portion of the papillomavirus genome. It has been discovered that the E2 mRNA of papillomaviruses is particularly suitable for this approach. In preferred embodiments, oligonucleotides are provided which are targeted to the mRNA CAP region and the translation codon for the E2 transactivator. For example, a 20-mer phosphorothioate oligonucleotide, ISIS 2105 (SEQ ID NO:7), targeted to the translation of initiation of both HPV-6 and HPV-11 E2 mRNA, covering nucleotides 2713 to 2732, has been found to inhibit E2-dependent transactivation in a concentration-dependent, sequence-specific manner.

DETAILED DESCRIPTION OF THE INVENTION

Genital warts are the most frequently diagnosed viral, sexually transmitted disease. Clinically, they may be categorized into two major groups: condyloma acuminata and flat cervical warts. Condylomas have been shown to contain virus particles and molecular studies have demonstrated that greater than 90% of these lesions contain either HPV-6 or HPV-11 DNA. Gissmann, L., Wolnik, L., Ikenberg, H., Koldovsky, U., Schnurch, H. G. & zur Hausen, H., *Proc. Natl. Acad. Sci. USA* 80:560–563 (1983). Condyloma acuminata generally occur on the penis, vulva or in the perianal region. They may spontaneously regress or persist for years and progression to an invasive carcinoma occurs only at a low frequency. Unlike other genital warts, those occurring on the uterine cervix usually exhibit a flat rather than acuminate morphology, and are usually clinically detected by Pap smear. A papillomavirus etiology for cervical dysplasia was suggested by the studies of cytologists in the late 1970s who demonstrated the association on Pap smear of cytologic changes due to HPV infection with those of dysplasia. Other studies showed the presence of viral particles and viral capsid antigen in some of the dysplastic cells of these lesions. This association was important because previous clinical studies had established that cervical dysplasia (also referred to as CIN, or cervical intraepithelial neoplasia) was a precursor to carcinoma in situ which was in turn recognized to be a precursor to invasive squamous epithelial cell carcinoma of the cervix. HPV-types 16 and 18 were cloned out directly from cervical carcinoma. Dürst, M., Gissmann, L., Ikenberg, H. & zur Hausen, H., *Proc. Natl. Acad. Sci. USA* 80:3812–3815 (1983); Boshart, M., Gissmann, L., Ikenberg, H., Kleinheinz, A., Scheurlen, W. & zur Hausen, H., *EMBO J.* 3:1151–1157 (1984). These were subsequently used as hybridization probes to show that greater than 70% of the human cervical carcinomas and the derived cell lines scored positive for the presence of either of these HPV types. Another 20% contain additional HPV-types such as HPV-31, HPV-33, and HPV-35.

Data collected from the National Therapeutic Index showed that in 1984 there were 224,900 first office visits for genital warts and 156,720 first office visits for genital herpes. The incidence of genital warts has steadily increased throughout the 1970s and 1980s, as was recently demonstrated by an epidemiological study in which the mean incidence from 1950 to 1978 reached a peak of 106.5 per 100,000 population. The prevalence of cervical HPV infection in women aged 25 to 55 proved to be 0.8%, but in 22 year old women it was 2.7%. Recent studies on cytologically normal women have demonstrated the incidence of latent infection to be 11%. Thus, there appears to be a latent stage of the disease which suggests an even greater incidence and prevalence.

Active genital warts can be identified in approximately 2.5% of pregnant American women, thus being implicated in 60,000 to 90,000 pregnancies annually. HPV infections are more than twice as prevalent in pregnant women. Each year there are an estimated 1,500 new cases of laryngeal papillomatosis, indicating that the risk of infection from mother to newborn is 1:80 to 1:200.

Laryngeal papillomas are benign epithelial tumors of the larynx. Two PV types, HPV-6 and HPV-11, are most commonly associated with laryngeal papillomas. Clinically, laryngeal papillomas are divided into two groups, juvenile onset and adult onset. In juvenile onset it is thought that the neonate is infected at the time of passage through the birth canal of a mother with a genital PV infection. Disease is usually manifest by age 2 and is characterized by the slow but steady growth of benign papillomas that will ultimately occlude the airway without surgical intervention. These children will typically undergo multiple surgeries with the papillomas always reoccurring. Patients will ultimately succumb to complications of multiple surgery. To date there is no curative treatment for juvenile onset laryngeal papillomatosis and spontaneous regression is rare. Adult onset laryngeal papillomatosis is not as aggressive and will frequently undergo spontaneous remission.

The most common disease associated with papillomavirus infection are benign skin warts. Common warts generally contain HPV types 1, 2, 3, 4 or 10. These warts typically occur on the soles of feet, plantar warts, or on the hands. Common skin warts are most often found in children and young adults. Later in life the incidence of common warts decreases presumably due to immunologic and physiologic changes. Plantar warts can often be debilitating and require surgical removal and they frequently reoccur after surgery. To date there is no reliable treatment for plantar warts. Common warts of the hands are unsightly but rarely become debilitating and are therefore not usually surgically treated.

Epidermodysplasia verruciformis (EV) is a rare genetically transmitted disease which is characterized by disseminated flat warts that appear as small reddish macules. A variety of HPV types have been associated with EV. With time approximately one third of EV patients develop squamous cell carcinoma (SCC) of the skin at multiple sites. In general, SCC occurs on sun exposed areas of the skin. Only a subset of EV associated PV is consistently found in SCC, HPV-5 and HPV-8. Genetic predisposition, immunologic abnormalities, and UV irradiation as well as HPV may all contribute to the development of SCC in these patients.

Figure 2:
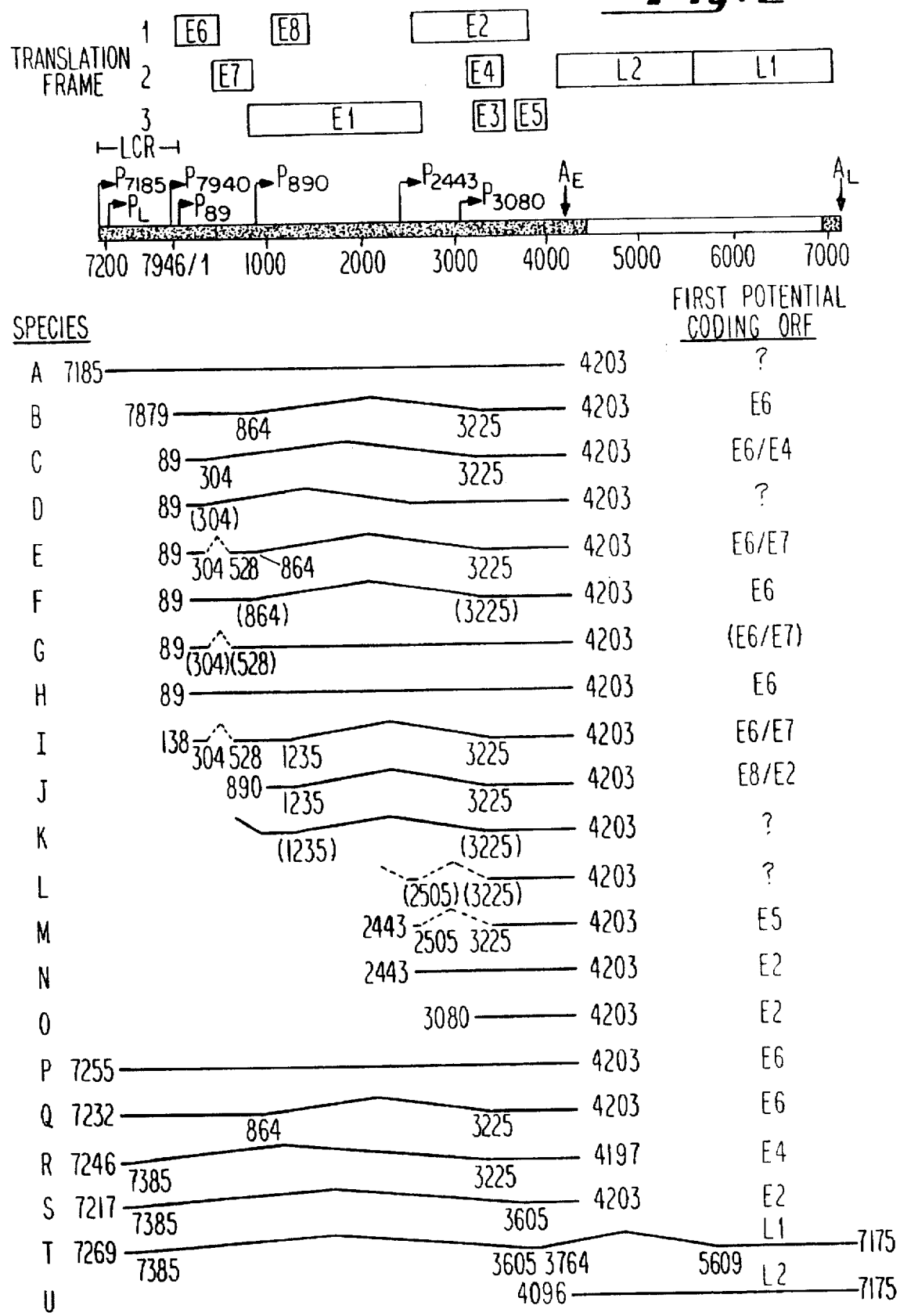
FIG. 2 is a partial genetic mapping of a bovine papillomavirus, BPV-1, genome showing open reading frames, ORFs, and messenger RNAs transcribed from the genome.

The PV genome consists of a double stranded, covalently closed, circular DNA molecule of approximately 8,000 base pairs. The complete nucleotide sequence and genetic organization of a number of animal and human PVs have been determined including bovine papillomavirus type 1 (BPV-1). Chen, E. Y., Howley, P. M., Levinson, A. D. & Seeburg, P. H., *Nature* 299:529–534 (1982). Schematic maps of several PV genomes are shown in FIG. 1. Viral transcription is unidirectional: all viral mRNAs are transcribed from the same strand of viral DNA. Engel, L. W., Heilman, C. A. & Howley, P. M., *J. Virol.* 47:516–528 (1983); Heilman, C. A., Engel, L., Lowy, D. R. & Howley, P. M., *Virology* 119:22–34 (1982). The coding strand contains 10 designated open reading frames (ORFs). The individual ORFs have been classified as either "early" or "late" ORFs based on their position in the PV genome and their pattern of expression in non-productively versus productively infected cells. FIG. 2 depicts the relationships of several ORFs for bovine papillomavirus-1.

Because of its ability to transform rodent cells and maintain its genome as an episome in transformed cells, BPV-1 has served as the model papillomavirus for in vitro studies. As a result, BPV-1 is the best characterized of all the papillomaviruses. The BPV-1 genome is 7946 base pairs in length and has been cloned and sequenced. Chen et al., 1982, supra. DNA sequence analysis of BPV-1 has defined 8 early (E) and 2 late (L) open reading frames (ORFs). Designation of ORFs as early or late was based on their pattern of expression in nonproductively infected transformed cells versus permissively infected cells. Heilman et al., 1982, supra; Baker, C. C. & Howley, P. M., *EMBO J.* 6:1027–1035 (1987).

All ORFs are contained on the same strand of DNA and all mRNAs currently characterized have been shown to be transcribed from the coding strand. Amtmann, E. & Sauer, G., *J. Virol.* 4:59–66 (1982). The functions of the BPV-1 ORFs have been analyzed by recombinant DNA techniques and in vitro cell culture systems. The full length E2 ORF encodes a protein which transactivates viral transcription. (Spalholz, B. A., Yang, Y. C. & Howley, P. M., *Cell* 42:183–191 (1985)) while the 3' E2 ORF encodes a transrepressor of viral transcription. Lambert, P. F., Spalholz, B. A. & Howley, P. M., *Cell* 50:69–78 (1987).

In accordance with this invention, persons of ordinary skill in the art will understand that messenger RNA identified by the open reading frames of the DNA from which they are transcribed include not only the information from the ORFs of the DNA, but also associated ribonucleotides which form regions known to such persons as the 5' cap region, the 5' untranslated region, and 3' untranslated region. Thus, oligonucleotides may be formulated in accordance with this invention which are targeted wholly or in part to these associated ribonucleotides as well as to the informational ribonucleotides.

It is to be expected that differences in the DNA of papillomaviruses from different species and from different types within a species exist. It is presently believed, however, that the similarities among the ORFs of the various PVs outweigh the differences. Thus, it is believed, for example, that the E2 regions of the various PVs serve essentially the same function for the respective PVs and that interference with expression of the E2 genetic information will afford similar results in the various species. This is believed to be so even though differences in the nucleotide sequences among the PV species may exist.

Accordingly, nucleotide sequences set forth in the present specification will be understood by those skilled in the art to be representational for the particular species being described. Homologous or analogous sequences for different species of papillomavirus targeted to the same region of the gene can be routinely determined by those of skill in the art upon this disclosure and are therefore within the scope of this invention.

Early genetic experiments showed that deletion or mutation of E2 resulted in loss of BPV focus forming activity on C127 cells suggesting a transforming function for E2. Later studies showed that E2 was a regulator of viral transcription and that loss of transforming ability by mutation of E2 was due to the down regulation of other transforming genes through E2 conditional enhances. The full length E2 ORF encodes the E2 transactivator which stimulates transcription of viral early genes. The E2 transactivator is translated from an unspliced mRNA whose 5' end maps to nt 2443 as shown as species N in FIG. 2. The E2 transrepressor is an N-terminally truncated form of the E2 transactivator, generated by initiation of transcription within the E2 ORF by a promoter at nt 3089. Species O, FIG. 2. The transactivating (5' portion) and DNA binding domains (3' portion) as well as the palindromic DNA recognition sequence (ACCN6GGT) of E2 have been identified. Both E2 mRNA and protein have been shown to have a very short half life, on the order of less than about 60 minutes. The E2 transregulatory circuit is a general feature among papilloma viruses. E2 transregulator has been documented in every papillomavirus examined to date.

The PV genome is packaged in a naked icosahedral capsid 55 nm in diameter. The viral capsid in nonenveloped and is not glycosylated. Two viral encoded proteins, designated L1 and L2, make up the capsid. L1 is the major capsid protein, constitutes 80% of the protein present in the virion, and has a molecular weight ranging between 50 to 60 kD. The L2 is a minor capsid protein with a theoretical molecular weight of 51 kD but has been shown to migrate at 76 kD. Because PV cannot be produced in vitro and very few mature virions are found in productive lesions, it has not been possible to do a detailed study of the serology of PV.

To date, no in vitro system that allows production of mature PV virions has been developed, and as a result, it has not been possible to characterize the life cycle of papillomaviruses. PV have a restricted host range rarely crossing species barriers. In addition PV infect only differentiating epithelium, either mucosal or keratinizing. Regulation of the PV gene expression is thought to be intimately linked to the differentiation program of host epithelial cells. The currently favored model of the PV life cycle is as follows: infectious PV particles penetrate the outer layers of the epithelium via trauma and infect the basal cells of host tissue. There the virus is maintained as a relatively low copy extrachromosomal element. As the epithelial cells begin to undergo differentiation, the PV genome is replicated to high copy number, as the cells begin to undergo the terminal stages of differentiation late genes are expressed and the viral genome is encapsulated.

Papillomavirus are ideal targets for oligonucleotide therapy. Papillomavirus lesions are external, allowing topical approaches for delivery of the oligonucleotides and eliminating many of the problems associated with systemic administration of many drugs. For compounds administered either intradermally or topically to the site of action, there is direct correlation between in vitro data and the in vivo situation. Direct administration to the site of action of the drug is the same as is seen in cell culture where a compound is added directly to the cell surface. External lesions also allow for easy access for tissue sampling for the diagnosis of specific types of papillomavirus using the oligonucleotides of the present invention.

It has been discovered that the E2 ORF on papillomavirus genomes is particularly well-suited for oligonucleotide targeting. E2 has been shown to be the major transactivator of viral transcription in both BPV-1 and HPV systems. Mutations in the E2 ORF have pleiotropic effects on transformation and extrachromosomal DNA replication. DiMaio, D., *J. Virol.* 57:475–480 (1986); DiMaio, D. & Settleman, J., *EMBO J.* 7:1197–1204 (1988); Groff, D. E. & Lancaster, W. D., *Virology* 150:221–230 (1986); Rabson, M. S., Yee, C., Yang, Y. C. & Howley, P. M., *J. Virol.* 60:626–634 (1986); and Sarver, N., Rabson, M. S., Yang, Y. C., Byrne, J. C. & Howley, P. M., *J. Virol.* 52:377–388 (1984). Subsequently, the E2 ORF has been shown to encode a transcriptional transactivator. Spalholz, B. A., Yang, Y. C. & Howley, P. M., *Cell* 42:183–191 (1985). A truncated version of E2 created by initiation of translation at an internal AUG has been shown to be a transrepressor of transcription. Lambert, P. F., Spalholz, B. A. & Howley, P. M., *Cell* 50:69–78 (1987). Both the DNA binding domain, the carboxy terminal 100 amino acids, (McBride, A. A., Schlegel, R. & Howley, P. M., *EMBO J.* 7:533–539 (1988)) and the DNA recognition sequence, (Androphy, E. J., Lowy, D. R. & Schiller, J. T., *Nature* 325, 70–73 (1987), and Moskaluk, C. & Bastia, D., *Proc. Natl. Acad. Sci. USA* 84:1215–1218 (1987)) have been identified. The E2 transcriptional regulatory circuit is a general feature among papillomaviruses. E2 transregulation has been documented in each of the other papillomaviruses examined to date. Gius, D., Grossman, S., Bedell, M. A. & Laimins, L. A., *J. Virol.* 62:665–672 (1988); Hirochika, H., Broker, T. R. & Chow, L. T., *J. Virol.* 61:2599–2606 (1987); Chin, M. T., Hirochika, R., Hirochika, H., Broker, T. R. & Chow, L. T., *J. Virol.* 62:2994–3002 (1988); Phelps, W. C. & Howley, P. M., *J. Virol.* 61:1630–1638 (1987); and Thierry, F. & Yaniv, M., *EMBO J.* 6:3391–3397 (1987).

It has now been determined that the identification of an obligatory viral transcription element that is shared among papillomaviruses causes E2 to be a prime target for oligonucleotides for papillomavirus research, diagnosis and therapy. For example, a 20-mer phosphorothioate oligonucleotide, ISIS 2105 (SEQ ID NO: 7), targeted to the AUG region of the HPV-11 E2 transactivator mRNA, covering nucleotides 2713 to 2732, was found to inhibit E2-dependent transactivation in a concentration-dependent, sequence-specific manner.

Recent experiments suggest that antisense oligonucleotides directed towards the 5' regions of mRNAs and preferably the cap region and the start codon are most effective in inhibiting gene expression. One feature of papillomavirus transcription is that many of the mRNAs have a common 5' untranslated region and cap. Thus it has been determined that antisense oligonucleotides directed towards this region have the potential to incapacitate more than one mRNA The shutting down of multiple viral genes will likely act at a minimum in an additive fashion and possibly synergistically in the eradication of the viral genome from the infected cell.

The present invention employs oligonucleotides for use in the diagnosis and treatment of papillomavirus. In the context of this invention, the term "oligonucleotide" refers to a polynucleotide formed from naturally-occurring bases and cyclofuranosyl groups joined by native phosphodiester bonds. This term effectively refers to naturally-occurring species or synthetic species formed from naturally-occurring subunits or their close homologs. The term "oligonucleotide" may also refer to moieties which function similarly to oligonucleotides, but which have non naturally-occurring portions. Thus, oligonucleotides may have altered sugar moieties or inter-sugar linkages. Exemplary among these are the phosphorothioate and other sulfur containing species which are known for use in the art. In accordance with some preferred embodiments, at least one of the phosphodiester bonds of the oligonucleotide has been substituted with a structure which functions to enhance the ability of the compositions to penetrate into the region of cells where the RNA whose activity is to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with structures which are, at once, substantially non-ionic and non-chiral, or with structures which are chiral and enantiomerically specific. Persons of ordinary skill in the art will be able to select other linkages for use in the practice of the invention.

Oligonucleotides may also include species which include at least some modified base forms. Thus, purines and pyrimidines other than those normally found in nature may be so employed. Similarly, modifications on the furanosyl portions of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, SCH$_3$, F, OCH$_3$, OCN, O(CH$_2$)$_n$NH$_2$ or O(CH$_2$)$_n$CH$_3$, where n is from 1 to about 10, and other substituents having similar properties.

Such oligonucleotides are best described as being functionally interchangeable with natural oligonucleotides or synthesized oligonucleotides along natural lines, but which have one or more differences from natural structure. All such analogs are comprehended by this invention so long as they function effectively to hybridize with messenger RNA of papillomavirus to inhibit the function of that RNA.

The oligonucleotides in accordance with this invention preferably comprise from about 3 to about 50 subunits. It is more preferred that such oligonucleotides comprise from about 8 to about 25 subunits and still more preferred to have from about 12 to about 20 subunits. As will be appreciated, a subunit is a base and sugar combination suitably bound to adjacent subunits through phosphodiester or other bonds. The oligonucleotides used in accordance with this invention may be conveniently and routinely made through the well-known technique of solid phase synthesis. Equipment for such synthesis is sold by several vendors, including Applied Biosystems. Any other means for such synthesis may also be employed, however, the actual synthesis of the oligonucleotides is well within the talents of the routineer. It is also well known to prepare other oligonucleotides such as phosphorothioates and alkylated derivatives.

The oligonucleotides of this invention are targeted to messenger RNA of papillomavirus. "Targeting" an oligonucleotide to the associated ribonucleotides, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is the human papillomavirus E2 transactivator region. The targeting process also includes determination of a site or sites within this region for the oligonucleotide interaction to occur such that the desired effect, either detection of the virus or modulation of expression of the virus, will result. Once the target site or sites have been identified, oligonucleotides are chosen which are sufficiently complementary to the target, i.e., hybridize sufficiently well and with sufficient specificity, to give the desired effect.

When the oligonucleotides of the present invention are used as therapeutics, such hybridization, when accomplished, interferes with the normal function of the messenger RNA to cause a loss of its utility to the virus. The functions of messenger RNA to be interfered with include all vital functions such as translocation of the RNA to the situs for protein translation, actual translation of protein from the RNA, and possibly even independent catalytic activity which may be engaged in by the RNA. The overall effect of such interference with the RNA function is to cause the papillomavirus to lose the benefit of the RNA and, overall, to experience interference with expression of the viral genome.

In accordance with the present invention, it is preferred to provide oligonucleotides designed to interfere with messenger RNAs determined to be of enhanced metabolic significance to the virus. As explained above, the E2 mRNA is the preferred target. It is also preferred to interfere with RNA coded by nucleotides substantially equivalent to nucleotides 2443 through 3080 of bovine papillomavirus-1 genome since these are believed to represent a particularly vulnerable situs for attack as this region is believed to code for a plurality of RNAs leading to essential proteins. It will be appreciated that differing papillomaviruses will have somewhat different structures from bovine papillomavirus-1, but that essentially similar areas may be routinely determined.

FIGS. 3a, 3b, and 4 represent the area on the bovine papillomavirus-1 genome and any oligonucleotide designed to interfere with RNA coded by their counterparts in particular papillomaviruses is believed to be especially useful in interfering with operation of those papillomaviruses. Exemplary oligonucleotides targeted at the E2 mRNA of bovine papillomavirus-1 are set forth in Table 1.

TABLE 1

BPV-1 E2 antisense oligonucleotides

| Oligo-nucleotide | 5'------------3' | Comments |
|---|---|---|
| 001(LC001.AB1) | AGGTTTGCACCCGACTATGCAAGTACAAAT | mRNA cap region (SEQ ID NO: 11) |
| 002(LC002.AB1) | TATGCAAGTACAAAT | mRNA cap region (SEQ ID NO: 12) |
| 003(LC003.AB1) | CGTTCGCATGCTGTCTCCATCCTCTTCACT | initiation of translation (SEQ ID NO: 13) |
| 004(LC004.AB1) | GCATGCTGTCTCCAT | initiation of translation (SEQ ID NO: 14) |
| 005(LC005.AB1) | AAATGCGTCCAGCACCGGCCATGGTGCAGT | transrepressor start (SEQ ID NO: 15) |
| 006(LC006.AB1) | AGCACCGGCCATGGT | transrepressor start (SEQ ID NO: 16) |
| 007(LC007.AB1) | CAATGGCAGTGATCAGAAGTCCAAGCTGGC | translational termination (SEQ ID NO: 17) |
| 008(LC008.AB1) | GCAGTGATCAGAAGT | translational termination (SEQ ID NO: 18) |
| 009(LC009.AB1) | ATTGCTGCAGCTTAAACCATATAAAATCTG | 3' untranslated region (SEQ ID NO: 19) |
| 010(LC010.AB1) | CTTAAACCATATAAA | 3' untranslated region (SEQ ID NO: 20) |
| 011(LC011.AB1) | AAAAAAAGATTTCCAATCTGCATCAGTAAT | 5' untranslated region (SEQ ID NO: 21) |
| 012(LC012.AB1) | AAGATTTCCAATCTG | 5' untranslated region (SEQ ID NO: 22) |
| 013(LC013.AB1) | CAGTGTCCTAGGACAGTCACCCCTTTTTTC | 5' coding region (SEQ ID NO: 23) |
| 014(LC014.AB1) | GGACAGTCACCCCTT | 5' coding region (SEQ ID NO: 24) |

TABLE 1-continued

BPV-1 E2 antisense oligonucleotides

| Oligo-nucleotide | 5'------------3' | Comments |
| --- | --- | --- |
| 015(LC015.AB1) | TGTACAAATTGCTGTAGACAGTGTACCAGT | mid coding region (SEQ ID NO: 25) |
| 016(LC016.AB1) | GCTGTAGACAGTGTA | mid coding region (SEQ ID NO: 26) |
| 017(LC017.AB1) | GTGCGAGCGAGGACCGTCCCGTACCCAACC | 3' coding region (SEQ ID NO: 27) |
| 018(LC018.AB1) | GGACCGTCCCGTACC | 3' coding region (SEQ ID NO: 28) |
| 019(LC019.AB1) | TTTAACAGGTGGAATCCATCATTGGTGGTG | 5' coding region (SEQ ID NO: 29) |
| 020(LC020.AB1) | GGAATCCATCATTGG | 5' coding region (SEQ ID NO: 30) |

Examplary oligonucleotides targeted to the translation initiation codon of HPV-11 are set forth in Table 2.

TABLE 2

Antisense Oligonucleotides Targeted to the Translation Initiation Codon of HPV-11

| Compound | 5'------------3' | SEQ ID NO: |
| --- | --- | --- |
| I2100 | GCTTCCATCTTCCTC | 1 |
| I2101 | GCTTCCATCTTCCTCG | 2 |
| I2102 | TGCTTCCATCTTCCTCG | 3 |
| I2103 | TGCTTCCATCTTCCTCGT | 4 |
| I2104 | TTGCTTCCATCTTCCTCGT | 5 |
| I2105 | TTGCTTCCATCTTCCTCGTC | 6 |

Thus, it is preferred to employ any of the twenty oligonucleotides set forth above or any of the similar oligonucleotides which persons of ordinary skill in the art can prepare from knowledge of the respective, preferred regions of the E2 ORF of a papillomavirus genome as discussed above.

It is not necessary that the oligonucleotides be precisely as described in the foregoing table or precisely as required by a slavish interpretation of the mapping of the papillomavirus genome. Rather, the spirit of this invention permits some digression from strict adherence to the genome structure and its literal "translation" into oligonucleotide. Modifications of such structures may be made, so long as the essential hybridizing function of the oligonucleotides results. Appropriate modifications for the oligonucleotides of the present invention can be routinely determined by those of skill in the art based upon results from in vitro screening assays taught herein.

Similarly, it will be appreciated that species variation among the various papillomaviruses occur. While the E2 is very similar from species to species, some differentiation occurs. Alteration in the oligonucleotides to account for these variations is specifically contemplated by this invention.

A preferred assay to test the ability of E2 specific antisense oligonucleotides to inhibit E2 expression was based on the well documented transactivation properties of E2. Spalholtz et al., *J. Virol.* 61:2128–2137 (1987). A reporter plasmid (E2RECAT) was constructed to contain the E2 responsive element, which functions as an E2 dependent enhancer. E2RECAT also contains the SV40 early promoter, an early polyadenylation signal, and the chloramphenicol acetyl transferase gene (CAT). Within the context of this plasmid, CAT expression is dependent upon expression of E2. The dependence of CAT expression on the presence of E2 has been tested by transfection of this plasmid into C127 cells transformed by BPV-1, uninfected C127 cells and C127 cells cotransfected with E2RECAT and an E2 expression vector.

Figure 7:
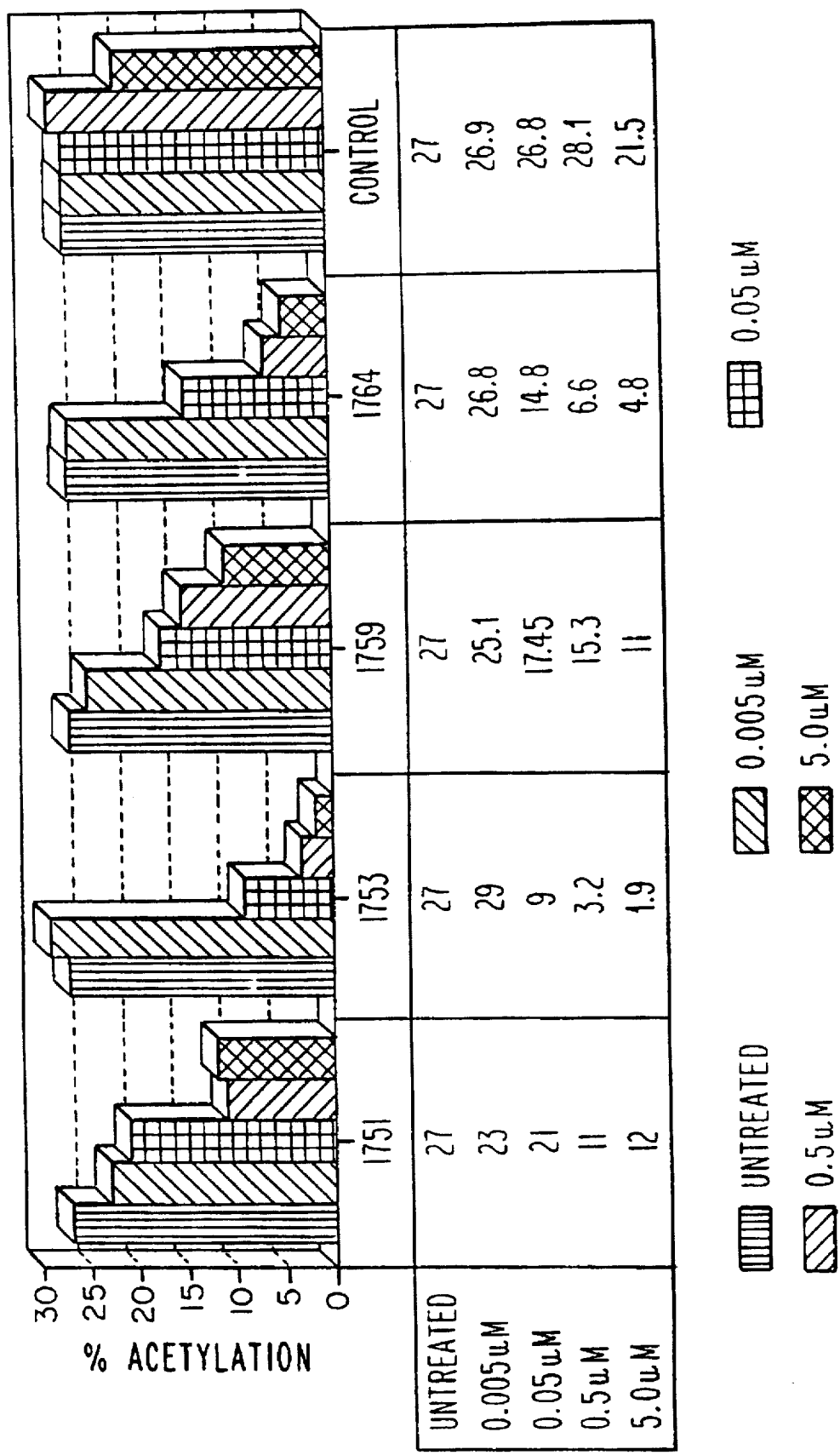
FIG. 7 is a graphical depiction of the dose response of antisense oligonucleotides made in accordance with the teachings of the invention. These dose response curves show that an antisense oligonucleotide, I1753, which is complementary to the E2 transactivation messenger RNA in the region including the translation initiation codon has an 50% inhibitory concentration (IC50) in the range of 50–100 nM while an oligonucleotide targeted to the CAP region of the same message (I1751) has an IC50 in the range of 500 nM.
Figure 9:
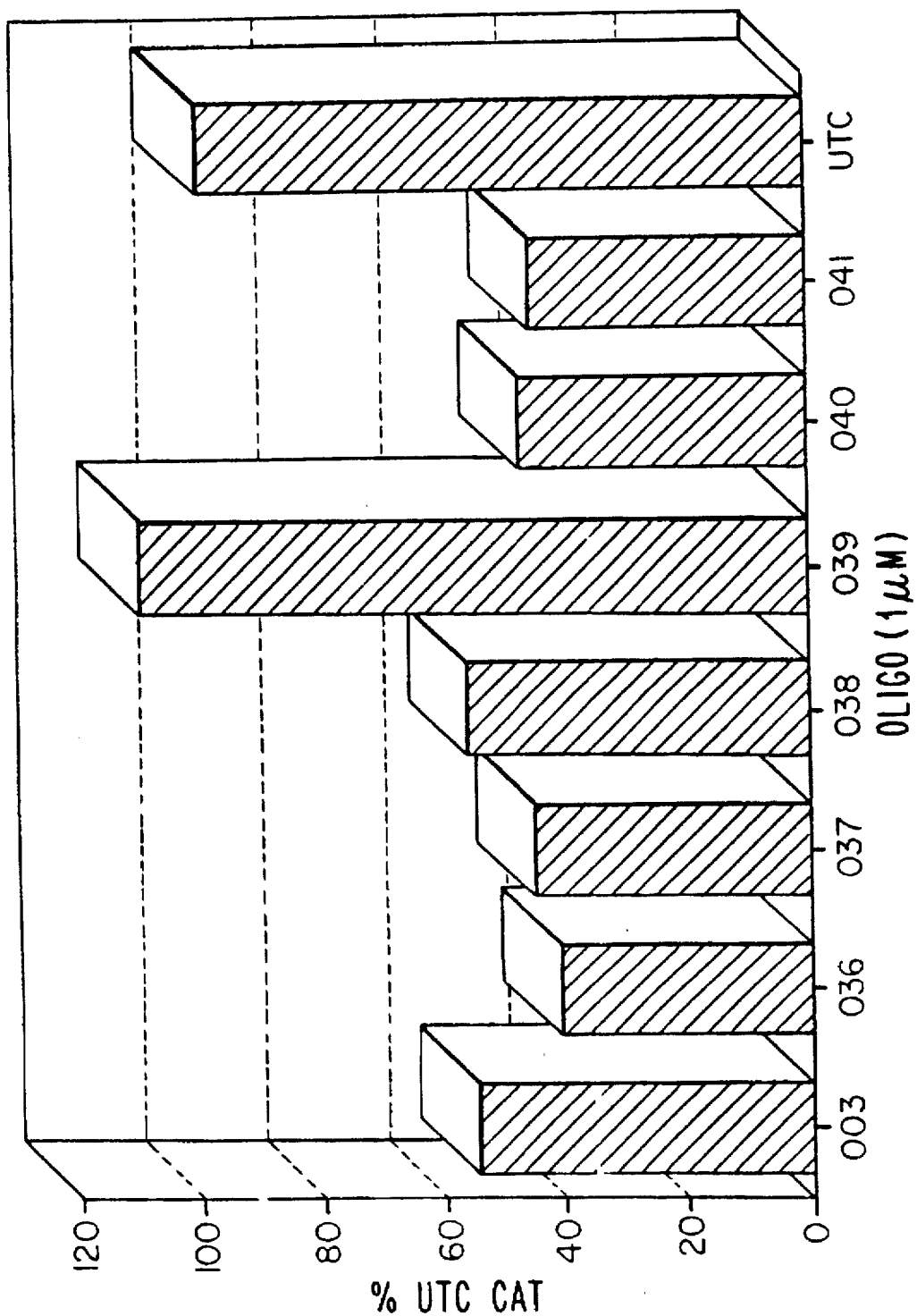
FIG. 9 is a graphical depiction of the effects of selected oligonucleotides targeted to the transactivator region of the E2 mRNA. The 15 to 20 mer antisense oligonucleotides made in accordance with the teachings of the invention are shown to inhibit E2 transactivation.
Figure 10:
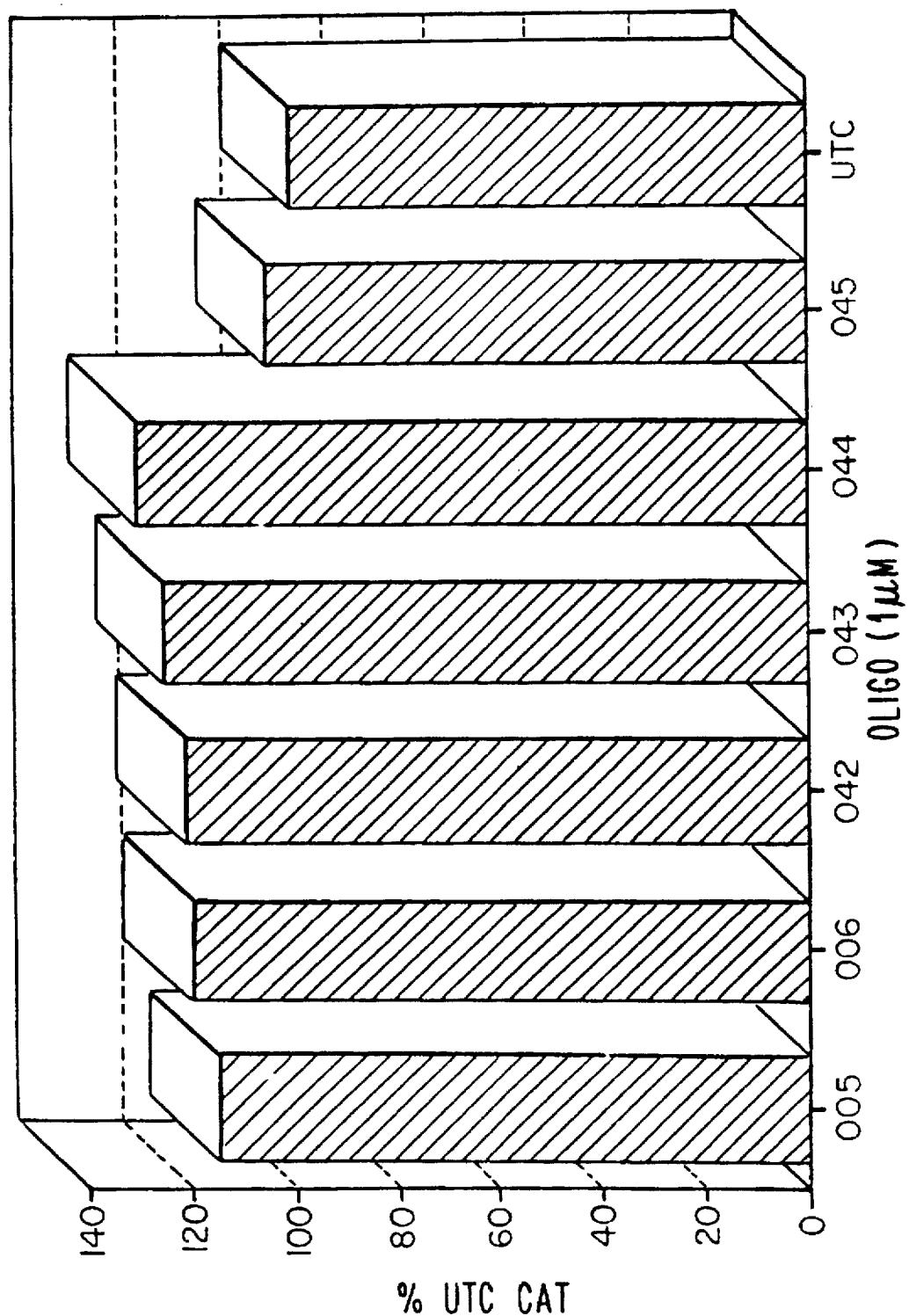
FIG. 10 is a graphical depiction of the effects of selected oligonucleotides targeted to the transrepressor region of the E2 mRNA. The 15 to 20 mer antisense oligonucleotides made in accordance with the teachings of the invention are shown to inhibit E2 transrepression.

Antisense oligonucleotides were designed to target the major E2 transactivator mRNA (FIG. 5). Targets included, but were not limited to, the mRNA CAP region, the translation initiation codon, translation termination codon, and polyadenylation signal. Fifteen or 30 residue oligonucleotides complementary to the various targets were synthesized with a wild type phosphodiester internucleosidic linkage or a modified phosphorothioate internucleosidic linkage. Oligonucleotides targeted to the mRNA CAP region (I1751) and the translation codon for the E2 transactivator (I1753) were shown to reduce E2 transactivation at 1 micromolar concentrations in preliminary screens (FIG. 6). Oligonucleotide I1756 targeted to the translation initiation codon of the E2 transrepressor (FIG. 5) was able to give partial relief of transrepression as demonstrated by an increase in CAT activity (FIG. 6). Other oligonucleotides of similar length and base composition, but targeted to other areas of the E2 mRNA, as well as other nonsense control, failed to give an antisense effect. In general, oligonucleotides with the phosphorothioate internucleosidic linkage modification were more effective than oligonucleotides of the same sequence containing the natural phosphodiester internucleosidic linkage. This is presumably due to the increased resistance of phosphorothioates to nucleases contained in the serum and within the cell. Dose response curves show that I1753 has an 50% inhibitory concentration (IC50) in the range of 50 to 100 nM while I1751 has an IC50 ten fold higher in the range of 500 nM (FIG. 7). After identification of the translation initiation codon of the E2 transactivator and transrepressor as successful antisense targets an additional set of phosphorothioates were designed to more carefully probe the regions (FIG. 8). These data showed that 15 to 20 mer oligonucleotides that covered the appropriate AUG could inhibit either E2 transactivation or transrepression (FIG. 9 and 10).

Figure 11:
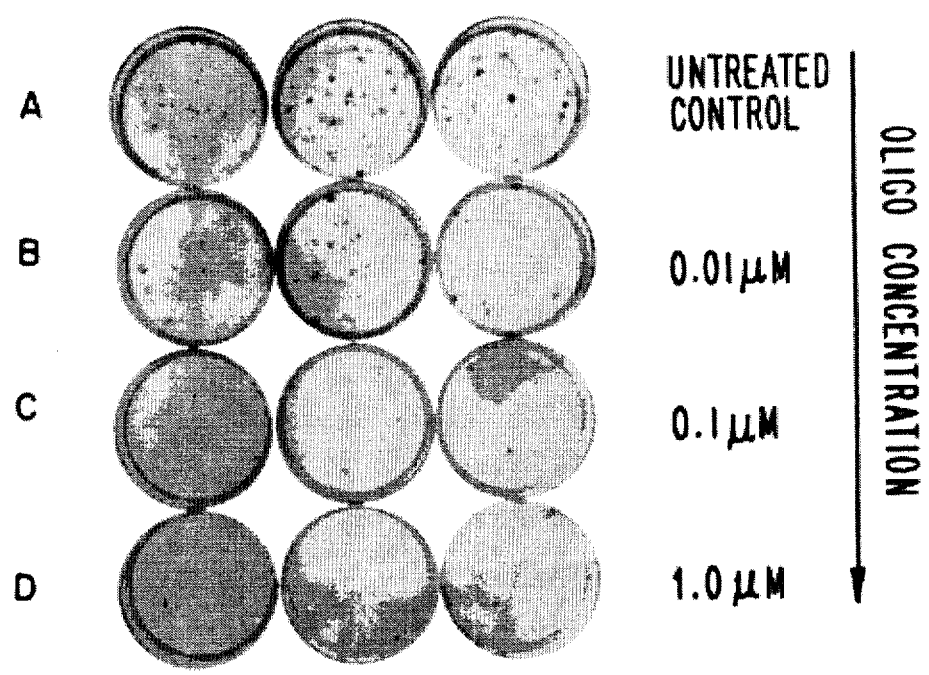
FIG. 11 is a photographic depiction of the consequences of reduction of E2 transactivator in situ on the biology of BPV-1. Antisense oligonucleotides made in accordance with the teachings of the invention were tested for the ability to inhibit or attenuate BPV-1 transformation of C127 cells. The photograph depicts petri dishes plated with test cells.
Figure 12:
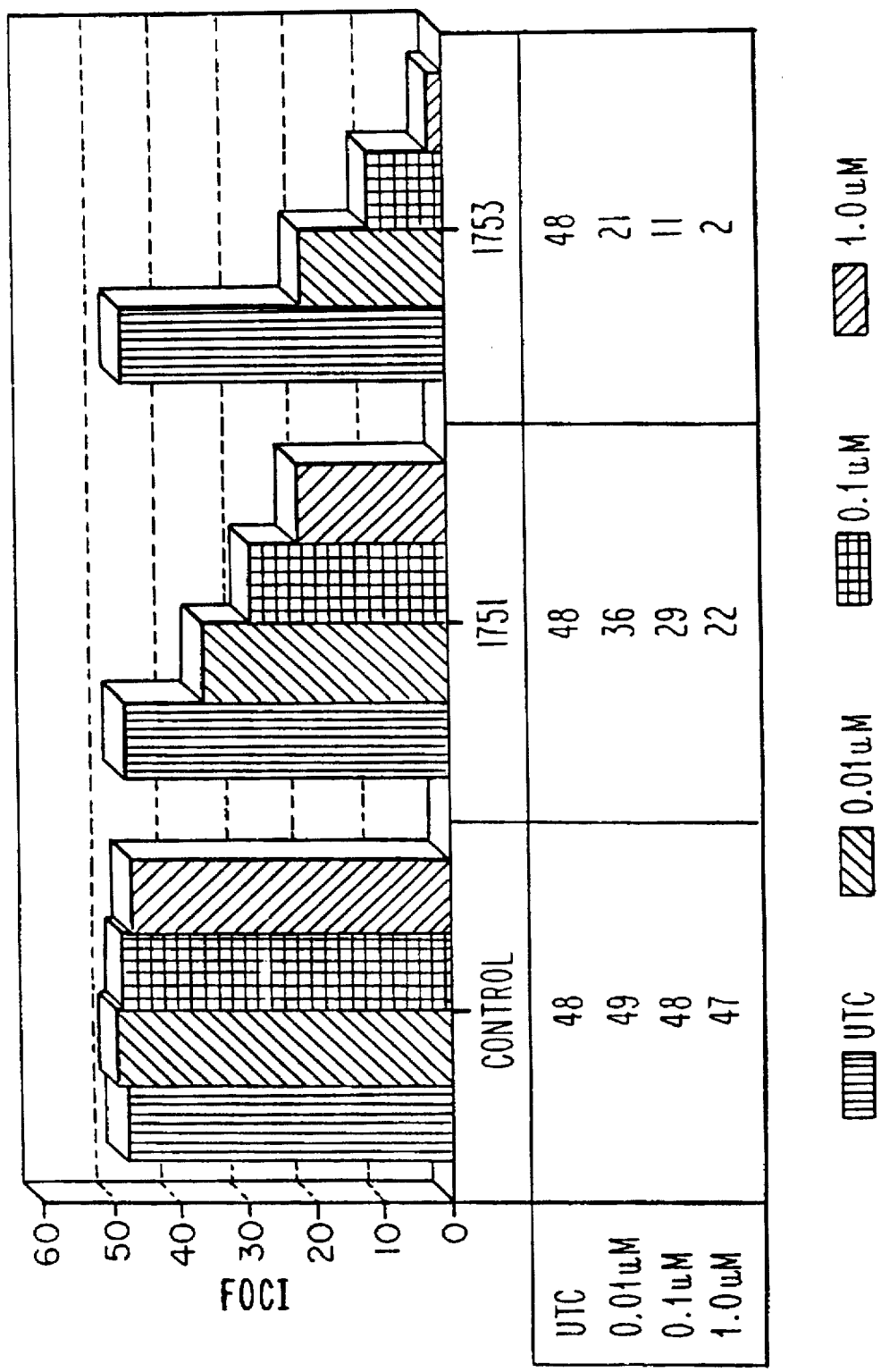
FIG. 12 is a graphical depiction of the effects of selected oligonucleotides targeted to the transactivator region of the E2 mRNA. The inhibition of BPV-1 focus formation by antisense oligonucleotides made in accordance with the teachings of the invention is depicted. These dose response curves for I1751 and I1753 show that I1753 had an IC50 in the range of 10 nM while I1751 had an IC50 in the range of 100 nM.

In order to determine the consequences of reduction of E2 transactivator in situ on the biology of the BPV-1, antisense oligonucleotides were tested for the ability to inhibit or attenuate BPV-1 transformation of C127 cells (FIG. 11). Dose response curves for I1751 and I1753 showed that I1753 had an IC50 in the range of 10 nM while I1751 had an IC50 in the range of 100 nM (FIG. 12).

Figure 13:
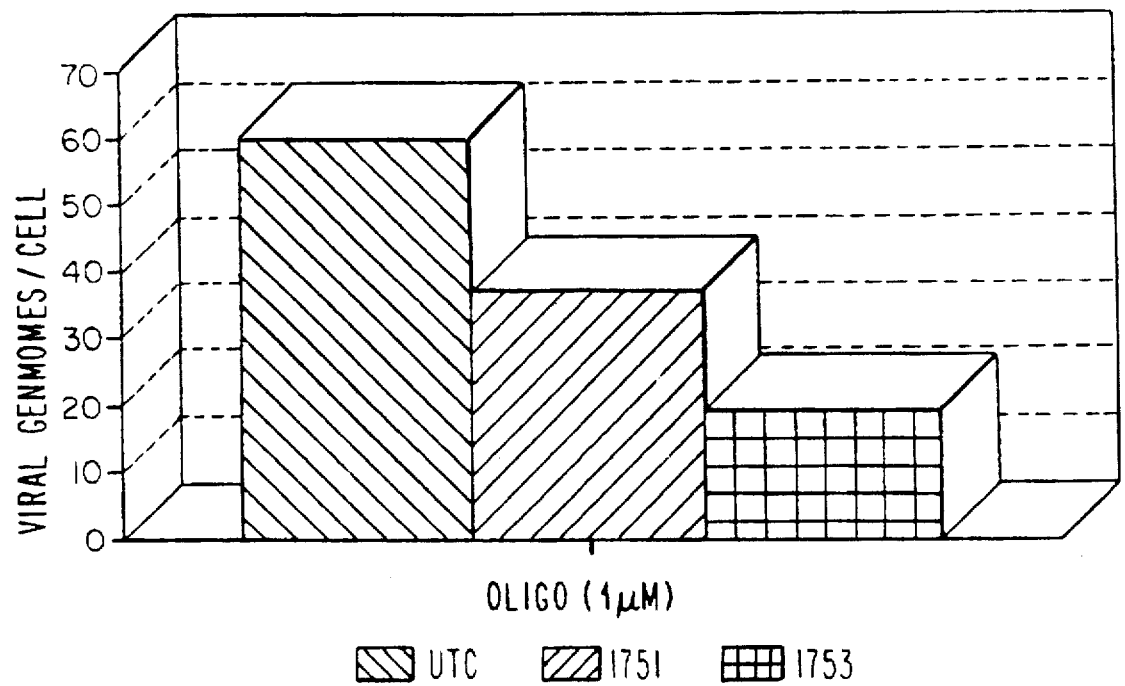
FIG. 13 is a graphical depiction of the effects of antisense oligonucleotides made in accordance with the teachings of the present invention on the ability of BPV-1 to replicate its genome. Cells transformed by the virus were treated with I1753 and I1751 and the viral DNA quantitated.

To test the effect of E2 targeted antisense oligonucleotides on the ability of BPV-1 to replicate, I-38 cells stably transformed by BPV-1 were treated with I1753 and I1751 and the viral DNA quantitated (FIG. 13). After 48 hours of treatment at 1 micromolar concentration the viral DNA copy number on a per cell basis was reduced by factor of approximately 3. During the course of this assay the cells divided between 2 and 3 times. This data suggests that the viral DNA failed to replicate synchronously with the cellular DNA.

Figure 14:
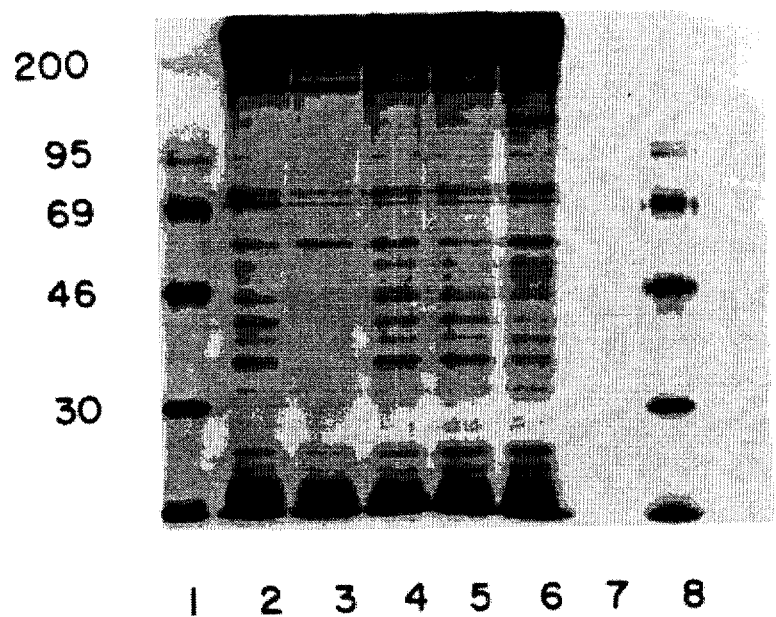
FIG. 14 shows the results of immunoprecipitation assays wherein metabolically labelled oligonucleotide-treated cells or untreated controls were immunoprecipitated using a monoclonal antibody.

In order to test the effect of I1753 on E2 protein synthesis, I-38 cells were metabolically labelled and immunoprecipitated with an E2 specific monoclonal antibody. In cells not exposed to oligonucleotide or cells treated with sense or irrelevant oligonucleotides the 46 kd E2 protein is present (FIG. 14). In cells treated with oligonucleotides targeted to the E2, the 46 kd band is lost suggesting that the oligonucleotide is operating by hybridization arrest of translation.

Figure 17:
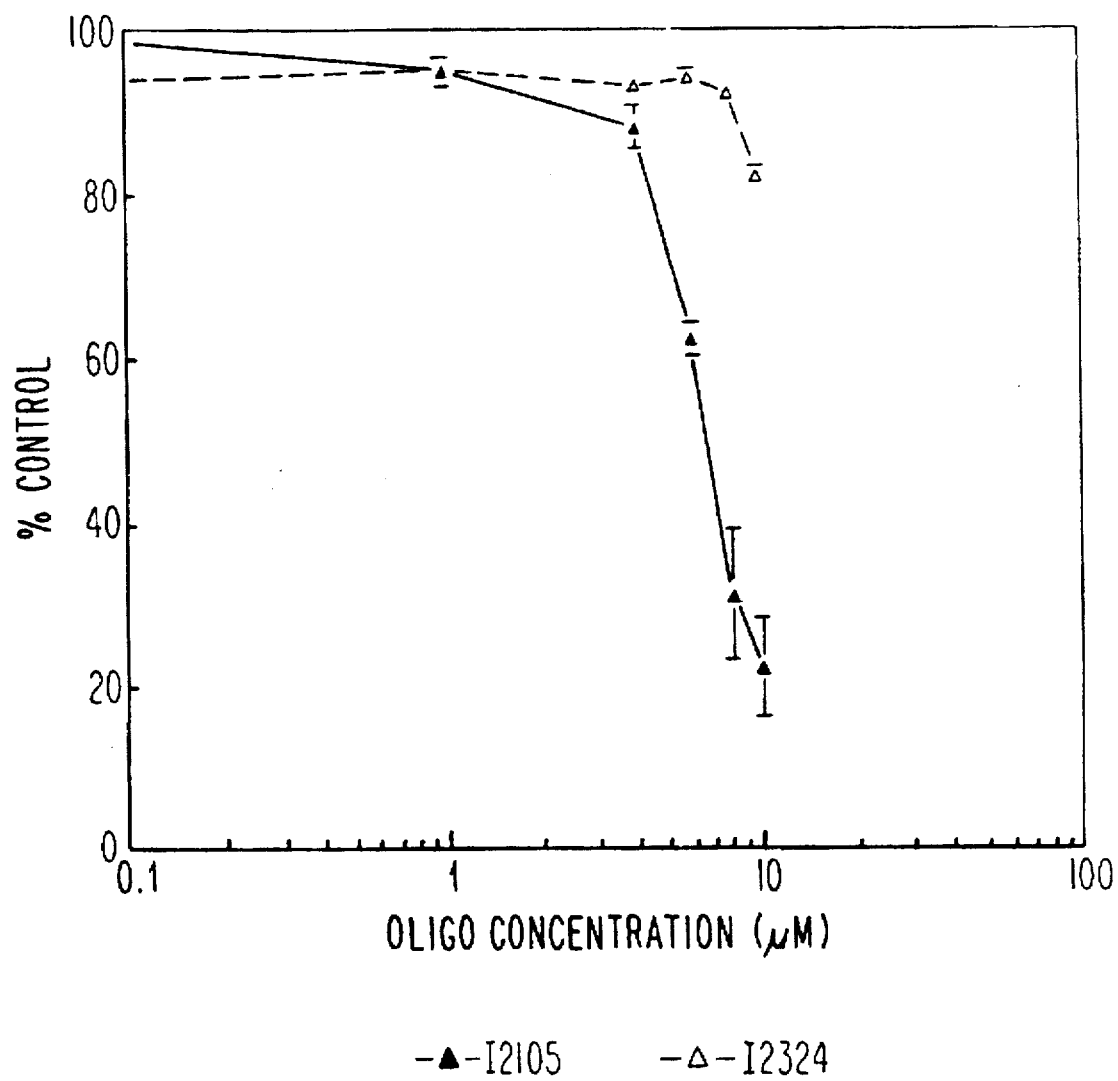
FIG. 17 is a graph showing inhibition of HPV-11 E2-dependent transactivation in a concentration-dependent sequence-specific manner by ISIS 2105, having an IC50 in the range of 5 µM.

Based on the BPV results obtained, oligonucleotides targeted to the human papillomavirus E2 transactivation region were synthesized. For example, a twenty nucleotide phosphorothioate oligonucleotide, ISIS 2105, was designed to hybridize to the AUG (translation initiation) region of the HPV-11 E2 transactivator mRNA. As was found with oligonucleotides targeted to BPV, ISIS 2105 was found to inhibit HPV-11 E2-dependent transactivation in a concentration-dependent sequence-specific manner with an IC50 in the range of 5 µM (FIG. 17). This demonstration of a pharmacological effect in cells is directly applicable to demonstrating therapeutic utility, especially in disease such as papillomavirus where no appropriate animal models are currently available. Such data are routinely requested and accepted by the Food and Drug Administration in determining whether studies can be conducted in humans. In fact this data was used to obtain approval to begin clinical trials with an oligonucleotide of the present invention.

A Phase II surgical adjuvant study with ISIS 2105 was performed. A total of 275 healthy men and women with condyloma acuminata (genital warts) were selected for the study. Condyloma acuminata (genital warts) were surgically removed and upon cessation of bleeding with electrocautery, skin surrounding the ablated area was injected with ISIS 2105 in phosphate buffered saline. It was shown that treatment with ISIS 2105 at either 0.3 mg or 1.0 mg dosage was found to be more effective than the placebo control at preventing wart recurrence after surgical ablation.

The oligonucleotides of this invention can be used in diagnostics, therapeutics and as research reagents and kits. For therapeutic use, the oligonucleotide is administered to an animal suffering from a papillomavirus infection such as warts of the hands, warts of the feet, warts of the larynx, condylomata acuminata, epidermodysplasia verruciformis, flat cervical warts, cervical intraepithelial neoplasia, or any other infection involving a papillomavirus. As with many other drugs, appropriate dose ranges to be administered in humans can be routinely determined by one of skill in the art based upon the IC50 determined by in vitro assays as described and fundamental principles of drug development. An illustration of this process is discussed by Agrawal and Sarin, *Adv. Drug Deliv. Rev.* (1991) 6:251–270. For example, in the case of ISIS 2105 wherein the IC50 is 5 µM and the molecular weight is 2459 g/l, the dose to be administered in humans must be greater than 0.012 mg/ml. Fundamental principles of pharmacology indicate that the administered dose in any in vivo study should be greater than the IC50 value. How much greater will depend upon the toxicity of the class of compounds being administered. It has been established that oligonucleotides are not highly toxic compounds (Iversen, P. 1991, *Anticancer Drug Des.* 6:531–538). Therefore doses tested in a range-finding human efficacy study should be larger than the IC50 value determined for that oligonucleotide in human cells. For example, for ISIS 2105, wherein the IC50 value demonstrated that the dose in human studies should be greater than 0.012 mg/ml, doses administered which were found to be effective were 0.3 mg or 1 mg of ISIS 2105 in 0.1 cc phosphate buffered saline. Appropriate doses for other oligonucleotides of the present invention can be calculated in a similar fashion.

It is generally preferred to apply the therapeutic agent in accordance with this invention topically or intralesionally. Other forms of administration, such as transdermally or intramuscularly, may be useful. Inclusion in suppositories may also be useful. Use of the oligonucleotides of this invention in prophylaxis is also contemplated. Such may be accomplished, for example, by providing the medicament as a coating in condoms and the like.

Use of pharmacologically acceptable carriers is also preferred for some embodiments. Pharmacologically acceptable carriers include, but are not limited to saline solutions and buffered solutions. Suitable pharmaceutically acceptable carriers are well known in the art and are described for example in Gennaro, Alfonso, Ed., *Remington's Pharmaceutical Sciences*, 18th Edition 1990. Mack Publishing Co., Easton, Pa., a standard reference text in this field. Pharmaceutical carriers may be selected in accordance with the intended route of administration and the standard pharmaceutical practice. For example, formulations for intralesional administration may include sterile aqueous solutions which may also contain buffers, diluents and other suitable additives. In clinical trials ISIS-2105, the oligonucleotide was dissolved in phosphate buffered saline and injected intralesionally.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual oligonucleotides, and can generally be estimated based on IC50's in in vitro studies.

The present invention is also useful in diagnostics and in research. Since the oligonucleotides of this invention hybridize to papillomavirus, sandwich and other assays can easily be constructed to exploit this fact. Provision of means for detecting hybridization of an oligonucleotide with papillomavirus present in a sample suspected of containing it can routinely be accomplished. Such provision may include enzyme conjugation, radiolabelling or any other suitable detection system. A number of assays may be formulated employing the present invention, which assays will commonly comprise contacting a tissue sample with a detectably labeled oligonucleotide of the present invention under conditions selected to permit hybridization and measuring such hybridization by detection of the label.

For example, radiolabeled oligonucleotides can be prepared by $^{32}P$ labeling at the 5' end with polynucleotide kinase. Sambrook et al., *Molecular Cloning. A Laboratory Manual*, Cold Spring Harbor Laboratory Press, 1989, Volume 2, pg. 10.59. Radiolabeled oligonucleotides are then contacted with tissue or cell samples suspected of being infected with papillomavirus and the sample is washed to remove unbound oligonucleotide. Radioactivity remaining in the sample indicates bound oligonucleotide (which in turn indicates the presence of papillomavirus) and can be quantitated using a scintillation counter or other routine means.

Viral infection can be detected in this way. Radiolabeled oligonucleotides of the present invention can also be used to perform autoradiography of tissues to determine the localization, distribution and quantitation of papillomavirus for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing papillomavirus. Quantitation of the silver grains permits expression of the virus to be detected and permits targeting of oligonucleotides to these areas.

Analogous assays for fluorescent detection of papillomavirus expression can be developed using oligonucleotides of the present invention which are conjugated with fluorescein or other fluorescent tag instead of radiolabeling. Such conjugations are routinely accomplished during solid phase synthesis using fluorescently labeled amidites or CPG (e.g., fluorescein-labeled amidites and CPG available from Glen Research, Sterling Va.).

Each of these assay formats is known in the art. One of skill could easily adapt these known assays for detection of papillomavirus expression in accordance with the teachings of the invention providing a novel and useful means to detect papillomavirus.

Kits for detecting the presence or absence of papillomavirus may also be prepared. Such kits include an oligonucleotide target to human papillomavirus E2 transactivator messenger RNA.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

The following examples are provided for illustrative purposes only and are not intended to limit the invention.

EXAMPLES

EXAMPLE 1

Inhibition of Expression of BPV-1 E2 by Antisense Oligonucleotides

BPV-1 transformed C127 cells are plated in 12 well plates. Twenty four hours prior to transfection with E2RE1 cells are pretreated by addition of antisense oligonucleotides to the growth medium at final concentrations of 5, 15 and 30 mM. The next day cells are transfected with 10 μg of E2RE1CAT by calcium phosphate precipitation. Ten micrograms of E2RE1CAT and 10 μg of carrier DNA (PUC 19) are mixed with 62 μl of 2M $CaCl_2$ in a final volume of 250 μl of $H_2O$, followed by addition of 250 μl of 2X HBSP (1.5 mM $Na_2PO_2$, 10 mM KCl, 280 mM NaCl, 12 mM glucose and 50 mM HEPES, pH 7.0) and incubated at room temperature for 30 minutes. One hundred microliters of this solution is added to each test well and allowed to incubate for 4 hours at 37° C. After incubation cells are glycerol shocked for 1 minute at room temperature with 15% glycerol in 0.75 mM $Na_2PO_2$, 5 mM KCl, 140 mM NaCl, 6 mM glucose and 25 mM HEPES, pH 7.0. After shocking, cells are washed 2 times with serum free DMEM and refed with DMEM containing 10% fetal bovine serum and antisense oligonucleotide at the original concentration. Forty eight hours after transfection cells are harvested and assayed for CAT activity.

For determination of CAT activity, cells are washed 2 times with phosphate buffered saline and collected by scraping. Cells are resuspended in 100 μl of 250 mM Tris-HCl, pH 8.0 and disrupted by freeze-thawing 3 times. Twenty four microliters of cell extract is used for each assay. For each assay, the following are mixed together in an 1.5 ml Eppendorff tube: 25 μl of cell extract, 5 μl of 4 mM acetyl coenzyme A, 18 μl $H_2O$ and 1 μl $^{14}C$-chloramphenicol, 40–60 mCi/mM and incubated at 37° C. for 1 hour. After incubation chloramphenicol (acetylated and nonacetylated forms) are extracted with ethyl acetate and evaporated to dryness. Samples are resuspended in 25 μl of ethyl acetate and spotted onto a TLC plate and chromatograph in chloroform:methanol (19:1). TLC are analyzed by autoradiography. Spots corresponding to acetylated and nonacetylated $^{14}C$-chloramphenicol are excised from the TLC plate and counted by liquid scintillation for quantitation of CAT activity. Antisense oligonucleotides that depress CAT activity in a dose dependent fashion are considered positives.

EXAMPLE 2

Inhibition of HPV E2 Expression by Antisense Oligonucleotides

The assay for inhibition of HPV E2 by antisense oligonucleotides is essentially the same as that for BPV-1 E2. For HPV assays appropriate HPVs are co-transfected into either CV-1 or A431 cells with PSV2NEO cells using the calcium phosphate method described above. Cells which take up DNA are selected for by culturing in media containing the antibiotic G418. G418 resistant cells are then analyzed for HPV DNA and RNA. Cells expressing E2 are used as target cells for antisense studies. For each antisense oligonucleotide cells are pretreated as above followed by transfection with E2RE1CAT and analysis of CAT activity as above. Antisense oligonucleotides are considered to have a positive effect if they can depress CAT activity in a dose dependent fashion.

EXAMPLE 3

Inhibition of HPV E7 Expression by Antisense Oligonucleotides

The E7 of HPV-16 has been shown to be capable of transactivating the Ad E2 promoter (Phelps, W. C. Yee, C. L., Munger, K., and Howley, P. M. 1988, The Human Papillomavirus Type 16 E7 Gene Encodes Transactivation and Transformation Functions Similar to Those of Adenovirus E1A, Cell 53:539–547. To monitor this activity, a plasmid is constructed which contained the chloramphenicol transferase gene under the control of the Ad E2 promoter (AdE2CAT). Under the conditions of this assay, CAT expression is dependent on expression of HPV E7. For this assay, cell lines are developed that contain the HPV E7 under the control of the SV40 early promoter. For each antisense oligonucleotide, cells are pretreated as above followed by transfection with AdE2CAT and analysis of CAT activity as above.

EXAMPLE 4

Inhibition of Expression of BPV-1 E1 by Antisense Oligonucleotides

The E1 of BPV-1 has been shown to be a regulator of viral genome replication. To test the effects of antisense oligonucleotides on viral replication C127 cells infected with BPV-1 are treated with E1 specific antisense oligonucleotides by addition of oligonucleotides to the growth medium at final concentrations of 5, 15 and 30 µM. The effects of the oligonucleotides are evaluated by a routine Northern blot analysis for quantitation of both E1 specific RNA as well as total viral RNA. In addition, the effects of antisense oligonucleotides on viral genome copy number are determined by Southern blot on total genomic DNA.

EXAMPLE 5

Determination of Efficacy of BPV-1 Antisense Oligonucleotides on Experimentally Induced Bovine Fibropapillomas Multiple bovine fibropapillomas are induce on calves by direct infection of the epidermis with purified BPV-1. Upon development, fibropapillomas are treated with oligonucleotides that had positive results in vitro as well as controls. Antisense oligonucleotides that induce regression of the fibropapilloma are considered as positives.

EXAMPLE 6

Design and Synthesis of Oligonucleotides Complementary to E2 mRNA

Antisense oligonucleotides were designed to be complementary to various regions of the E2 mRNA as defined by the published nucleotide sequence of BPV-1 (Chen, E. Y., Howley, P. M., Levinson, A. D., and Seeburg, P. H., The primary structure and genetic organization of the bovine papillomavirus type 1 genome, Nature 299:529-534 (1982)) and cDNA structure of the major E2 transactivator mRNA (Yang, Y. C., Okayama, H., and Howley, P. M., Bovine papillomavirus contains multiple transforming genes, Proc. Natl. Acad. Sci. USA 82:1030-1034 (1985)). Antisense oligonucleotides targeted to the translation initiation codon of HPV-11 E2 were based on the published sequence of HPV-11 (Dartmann, K., Schwarz, E., Gissamnn, L., and zur Hausen, Virology 151:124-130 (1986)). Solid-phase oligodeoxyribonucleotide syntheses were performed using an Applied Biosystems 380B automated DNA synthesizer. For the phosphorothioate oligonucleotides, sulfurization was performed after each coupling using 0.2M 3H-1,2-Benzodithiol-3-one-1,1-dioxide dissolved in acetonitrile as described by Iyer et al. (Iyer, R. P., Phillips, L. R., Egan, W., Regan, J. and Beaucage, S. L., The Automated Synthesis of Sulfur-Containing Oligodeoxyribonucleotides Using $^3$H-1, 2-Bensodithiol-3-one 1,1-Dioxide as a Sulfur-Transfer Reagent, J. Org. Chem. 55:4693-4699 (1990)). To insure complete thioation, the growing oligonucleotide was capped after each sulfurization step. After cleavage from the synthesis matrix, deprotection and detriylation oligonucleotides were ethanol precipitated twice out NaCl and suspended in water. The concentration of oligonucleotide was determined by optical density at 260 nm. For use in cell culture assays, oligonucleotides were routinely diluted to 100 micromolar stocks and stored at −80° C. until use. The purity, integrity, and quantity of the oligonucleotide preparations were determined by electrophoresis on 20% acrylamide 7M urea gels (40 cm × 20 cm × 0.75 mm) prepared as described by Maniatis et al. (Maniatis, T., Fritsch, E. F. and Sambrook, J. Molecular Cloning: A Laboratory Manual, Cold Spring Harbor Laboratory, New York, 1982). Electrophoresed oligonucleotides were visualized within the gel by staining with "Stains-all", 1-ethyl-2[3-(1-ethylnapthol[1,2-d]-thiazolin-2-ylidene)-2-Methyl-Propenyl[napthol[1,2d]-thiazolium bromide purchased from Sigma, E-9379, (Dahlberg, A. E., Digman, C. W. and Peacock, A. C., J. Mol. Biol. 41:39 (1969)).

EXAMPLE 7

Molecular Constructs

The E2 chloramphenicol acetyl transferase (CAT) reporter plasmid used in this study has been previously described (Spalholz, B. A., Byrne, J. C. and Howley, P. M., Evidence for Cooperativity between E2 Binding Sites in E2 trans-regulation of Bovine Papillomavirus Type 1, J. Virol. 62:3143-3150 (1988)). Briefly, the E2 responsive element, E2RE1; (nt 7611-7806) of BPV-1 was reconstructed using oligonucleotides and cloned into pSV2CAT that had been deleted of the SV40 enhancer, Sph1 fragment. Expression of CAT from this plasmid has been shown to be dependent upon full length E2. Plasmid C59 contain an E2 cDNA expressed from the simian virus 40 promoter and enhancer and has been described in detail elsewhere (Yang, Y.-C., Okayama, H. and Howley, P. M., Bovine papillomavirus contains multiple transforming genes, Proc. Natl. Acad. Sci. USA 82:1030-1034 (1985)). Two HPV-11 full length E2 expression constructs were made. IPV115 contains the XmnI fragment of HPV-11 (nt 2665-4988) cloned into the SmaI site of pMSG purchased from Pharmacia (catalog number 27-4506). IPV118 contains the same HPV-11 XmnI fragment cloned into the SmaI site of pSVL (Pharmacia, catalog number 27-4509).

EXAMPLE 8

Cell Lines

Mouse C127 cells (Dvoretzky, I. Schober, R., and Lowy, D., Focus Assay in Mouse Cells for Bovine Papillomavirus type 1, Virology 103:369-375 (1980)) were grown in Dulbecco's Modified Eagle's medium supplemented with 10% fetal bovine serum, penicillin (100 U/ml), streptomycin (100 µg/ml), and L-glutamine (4 mM). I-38 cell line was derived from a single focus of C127 cells transformed by purified BPV-1 (Cowsert, L. M., Lake, P., and Jenson, A. B., Topographical and conformational Epitopes of Bovine Papillomavirus type 1 Defined by Monoclonal Antibodies, JNCI 79:1053-1057 (1987)).

EXAMPLE 9

Oligonucleotide Inhibition of E2 Dependent Transactivation Assays

To test an oligonucleotide's ability to inhibit E2 transactivation or transrepression, I-38 cells were plated at 1×10$^4$ cells per cm$^2$ in 60 mm petri dishes 24 hours before transfection. Sixteen hours prior to transfection, media was aspirated and replaced with media containing oligonucleotide at the appropriate concentration. One hour prior to transfection, media was aspirated and replaced with fresh media without oligonucleotide. Cells were transfected by the calcium phosphate precipitation method as described by Graham et al. 1973 (Graham, F. L. and van der Eb, A. J., A New Technique for the Assay of Infectivity of Human Adenovirus 5 DNA, Virology 52:456-461 (1973)) with a total of 20 micrograms of DNA in one milliliter of precipitate. Each 60 mm dish received 200 microliters of precipitate containing 4 mictograms of DNA. Four hours after the addition of precipitated DNA, the supernatant was aspirated and the cells treated with 15% glycerol (Frost, E. and Williams, J., Mapping Temperature-Sensitive and host-range mutation of Adenovirus type 5 by Marker Rescue, Virology 91:39-50 (1978)). After washing, cells were refed with media containing oligonucleotide at the original concentration and incubated for 48 hours.

EXAMPLE 10

Antisense Oligonucleotide Inhibition of Focus Formation

The ability of antisense oligonucleotides that inhibited E2 transactivation to inhibit viral focus formation, a measure of transformation, was tested. Mouse C127 cells were plated at subconfluence ($5 \times 10^4$ cells/cm$^2$) in 60 mm petri dishes. Cells were either infected with 50 focus forming units (FFU) per plate of purified BPV-1 or transfected with cloned BPV-1 DNA. Twenty-four hours after infection or transfection, oligonucleotides were added to the medium. Medium was changed every 72 hours with fresh oligonucleotide added with each change. Twenty-five days post infection, cells were fixed in 10% formalin in PBS for 5 minutes and stained with 0.14% methylene blue aqueous solution-for 10 minutes. Plates were washed with water and foci counted.

Figure 16:
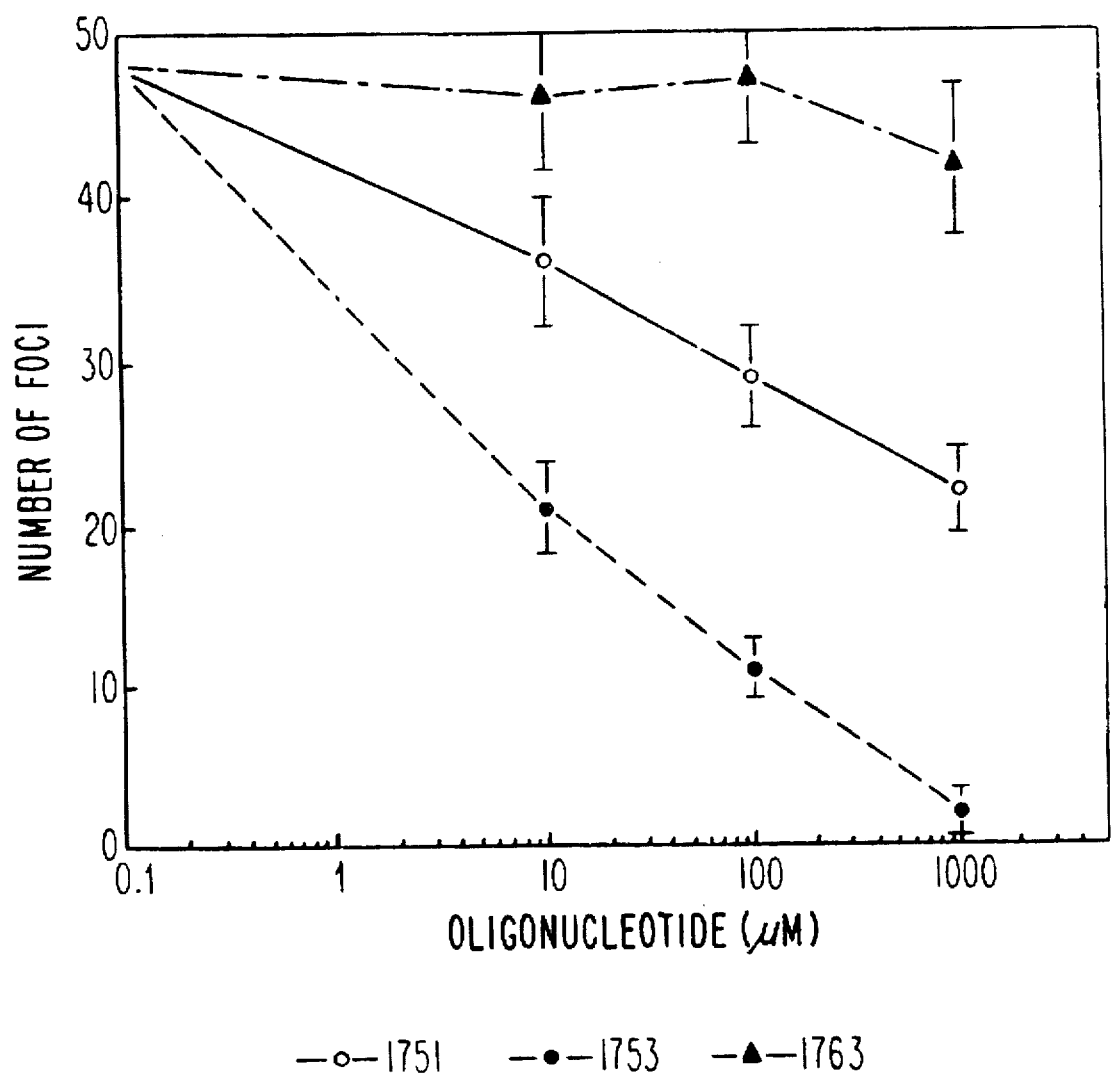
FIG. 16 is a graph showing that ISIS 1751 and ISIS 1753 inhibited BPV-1 focus formation on C127 cells.

The two compounds that inhibited E2 transactivation, ISIS 1751 and ISIS 1753, also inhibited BPV-1 focus formation on C127 cells (FIG. 16).

This effect was found to be concentration-dependent with an IC50 of 10 nM for ISIS 1753. A clear IC50 for ISIS 1751 was not achieved, but appears to be in the range of 500 to 1000 nM. ISIS 1755, which increased E2-dependent transactivation, had no effect on BPV-1 focus formation.

EXAMPLE 11

Antisense Oligonucleotide Inhibition of Human Papillomavirus HPV-11 E2 Transactivation Based on the BPV results obtained, a twenty nucleotide phosphorothioate oligonucleotide, ISIS 2105, was designed to hybridize to the AUG (translation initiation) region of the HPV-11 E2 transactivator mRNA. For inhibition of HPV-11 E2 transactivation, C127 cells were pretreated with oligonucleotide by addition to the medium. The next day, medium was aspirated and replaced with fresh medium without oligonucleotide. Cells were co-transfected with 2 µg IPV 118 HPV-11 E2 expression plasmid, 2 µg IPV120-15 D2-CAT reporter plasmid, and 2 µg PCH110. Following transfection, cells were treated again with oligonucleotide and incubated for 48 hours. Cells were harvested and processed for CAT and β-galactosidase assays. Chloramphenicol acetyltransferase activity was determined using standard protocols [Groman, C. M., Moffat, L. F., and Howard, B. H., *Mol. Cell. Biol.* 2:1044–1051 (1982)]. Acetylated and nonacetylated reaction products were separated by thin layer chromatography and quantitated using a Molecular Dynamics PhosphoImager (Molecular Dynamics, Sunnyvale Calif.). β-galactosidase activity was determined using standard methods [Herbomel et al., *Cell* 39:653 (1984)].

ISIS 2105 was found to inhibit HPV-11 E2-dependent transactivation in a concentration-dependent sequence-specific manner with an IC50 in the range of 5 µM (FIG. 17). ISIS 2324, a BPV-1 E2-specific oligonucleotide, did not inhibit HPV-11 E2 transactivation significantly. This is expected based on lack of sequence homology.

EXAMPLE 12

Clinical Trials with ISIS 2105

A Phase II surgical adjuvant study of ISIS 2105 (afovirsen) has been performed. A total of 275 healthy men and women with condyloma acuminata (genital warts) were selected for the study. Condyloma acuminata (genital warts) measuring at least 1×1 mm were surgically removed. Upon cessation of bleeding with electrocautery, skin surrounding the ablated area was injected with 0.1 cc of phosphate buffered saline vehicle containing 0.3 mg or 1 mg of ISIS 2105. Multiple warts per patient were treated. The efficacy results obtained at the six-month follow-up visit are presented in Table 3.

TABLE 3

ISIS 2105 EFFICACY RESULTS FOR SIX-MONTH FOLLOW-UP INTERVAL

| Efficacy Parameter | Statistic | ISIS-2105 (0.3 mg) | ISIS-2105 (1.0 mg) | Vehicle Control |
|---|---|---|---|---|
| Total Number of Patients | | 113 | 108 | 54 |
| Recurrence Incidence | | 14 (12%) | 14 (13%) | 8 (15%) |
| Days to Recurrence | n | 14 | 14 | 8 |
| | Median | 73 | 80 | 95 |
| | Mean | 84.7 ± 15.1 | 86.4 ± 12.2 | 96.1 ± 14.5 |
| | Min, Max | 14, 192 | 26, 176 | 29, 173 |
| Wart Recurrence | | 21 (7%) | 20 (6%) | 12 (9%) |

"Recurrence incidence" refers to the number of patients with at least one ablated and treated wart that recurred on or before the six-month follow-up visit. Includes early withdrawals from study without recurrence. "Days to recurrence" refers to ablated and treated wart-free time period in days. Wart recurrence refers to overall number of warts that recurred on or before the six-month follow-up visit. Includes early withdrawals from study without recurrence.

Table 3 reflects the final analysis of the six-month follow-up efficacy data after closure of the study. Treatment with ISIS 2105 at either 0.3 mg or 1.0 mg dosage was found to be more effective than the placebo control at preventing wart recurrence after surgical ablation. In patients treated with the higher dose of ISIS 2105, only 6% of warts recurred within six months. At the lower dose of ISIS 2105, 7% of warts recurred. In the placebo-treated group, the wart recurrence rate was found to be 9%, which is several fold lower than previously reported in the literature. Because of the unexpectedly low placebo recurrence rate, the study failed to show a statistically significant difference between placebo and treatment groups in this initial study. However, based on the efficacy shown in this study, a multiple-dose Phase II study of ISIS 2105 for treatment of genital warts caused by human papillomavirus is planned.

While a number of specific embodiments have been set forth, the present invention is to be limited only in accordance with the following claims.

What is claimed is:

1. An oligonucleotide consisting of from 8 to 50 nucleotides fully complementary to a translation initiation region of human papillomavirus E2 transactivator messenger RNA of HPV-6 or HPV-11.

2. A method of diagnosing papillomavirus infection by HPV-6 or HPV-11 in a cell or tissue sample comprising:

(a) labeling an oligonucleotide of claim 1 with a detectable label;

(b) contacting a cell or tissue sample suspected of being infected with HPV-6 or HPV-11 with the detectably labeled oligonucleotide under conditions which permit specific hybridization of the detectably labeled oligonucleotide to a target messenger RNA of HPV-6 or HPV-11; and (c) detecting the label of the hybridized oligonucleotide to determine the presence of HPV-6 or HPV-11 in the cell or tissue.

3. An oligonucleotide consisting of SEQ ID NO: 1, 2, 3, 4, 5 or 6.

4. A method of diagnosing papillomavirus infection by HPV-6 or HPV-11 in a cell or tissue sample comprising:

(a) labeling an oligonucleotide of claim 3 with a detectable label;

(b) contacting a cell or tissue sample suspected of being infected with HPV-6 or HPV-11 with the detectably labeled oligonucleotide under conditions which permit specific hybridization of the detectably labeled oligonucleotide to a target messenger RNA of HPV-6 or HPV-11; and (c) detecting the label of the hybridized oligonucleotide to determine the presence of HPV-6 or HPV-11 in the cell or tissue.

* * * * *

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 1:

GCTTCCATCT TCCTC                                             15

( 2 ) INFORMATION FOR SEQ ID NO: 2:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 2:

GCTTCCATCT TCCTCG                                         16

( 2 ) INFORMATION FOR SEQ ID NO: 3:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 3:

TGCTTCCATC TTCCTCG                                      17

( 2 ) INFORMATION FOR SEQ ID NO: 4:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 4:

TGCTTCCATC TTCCTCGT                                     18

( 2 ) INFORMATION FOR SEQ ID NO: 5:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 5:

TTGCTTCCAT CTTCCTCGT                                                               19

(2) INFORMATION FOR SEQ ID NO: 6:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 6:

TTGCTTCCAT CTTCCTCGTC                                                              20

(2) INFORMATION FOR SEQ ID NO: 7:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 7:

TTGCTTCCAT CTTCCTCGTC                                                              20

(2) INFORMATION FOR SEQ ID NO: 8:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 8:

AGCGCGCCAT AGTATTGTGG                                                              20

(2) INFORMATION FOR SEQ ID NO: 9:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 9:

GTCCATGCAT ACTTAATATT                                                              20

(2) INFORMATION FOR SEQ ID NO: 10:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 10:

TATTACGTAC TAGATTCTAC                                                              20